United States Patent
Duthie et al.

(10) Patent No.: US 11,268,116 B2
(45) Date of Patent: *Mar. 8, 2022

(54) ENDONUCLASE-ASSISTED ISOTHERMAL AMPLIFICATION USING CONTAMINATION-FREE REAGENTS

(71) Applicant: Global Life Sciences Solutions Operations UK Ltd, Sheffield (GB)

(72) Inventors: Robert Scott Duthie, Schenectady, NY (US); John Richard Nelson, Clifton Park, NY (US); Anuradha Sekher, Hillsborough, NJ (US)

(73) Assignee: GLOBAL LIFE SCIENCES SOLUTIONS OPERATIONS UK LTD, Sheffield (GB)

( * ) Notice: Subject to any disclaimer, the term of this patent is extended or adjusted under 35 U.S.C. 154(b) by 935 days.

This patent is subject to a terminal disclaimer.

(21) Appl. No.: 15/941,057

(22) Filed: Mar. 30, 2018

(65) Prior Publication Data

US 2019/0062795 A1     Feb. 28, 2019

Related U.S. Application Data

(60) Continuation of application No. 13/965,696, filed on Aug. 13, 2013, now abandoned, which is a continuation-in-part of application No. 13/330,745, filed on Dec. 20, 2011, now Pat. No. 9,951,379, which is a division of application No. 11/621,703, filed on Jan. 10, 2007, now Pat. No. 8,202,972.

(51) Int. Cl.
| | |
|---|---|
| *C12Q 1/68* | (2018.01) |
| *C12P 19/34* | (2006.01) |
| *C12Q 1/6844* | (2018.01) |
| *C12Q 1/6848* | (2018.01) |

(52) U.S. Cl.
CPC ............ *C12P 19/34* (2013.01); *C12Q 1/6844* (2013.01); *C12Q 1/6848* (2013.01)

(58) Field of Classification Search
None
See application file for complete search history.

(56) References Cited

U.S. PATENT DOCUMENTS

| | | | | |
|---|---|---|---|---|
| 6,291,161 B1* | 9/2001 | Lerner | .................. | C07K 16/00 435/235.1 |
| 7,993,839 B2* | 8/2011 | Nelson | ................. | C12Q 1/6848 435/6.12 |
| 2004/0067559 A1* | 4/2004 | McCarthy | ........ | C12Q 2531/119 435/91.2 |

FOREIGN PATENT DOCUMENTS

| | | | | |
|---|---|---|---|---|
| JP | H09-107997 A | 4/1997 | | |
| JP | 2008-048725 A | 3/2008 | | |
| JP | 2008-541705 A | 11/2008 | | |
| JP | 2015-526069 A | 9/2015 | | |
| WO | WO-2006125267 A1 * | 11/2006 | ........... | C12Q 1/6865 |
| WO | 2008/086381 A2 | 7/2008 | | |
| WO | 2009/077411 A1 | 6/2009 | | |
| WO | 2015022359 A1 | 2/2015 | | |

OTHER PUBLICATIONS

Machine Translation and Notification of Reasons for Refusal issued in connection with corresponding JP Application No. 2016-533915 dated Jun. 26, 2018.
Japanese Office Action for JP Application No. 2019-0966038 dated Jun. 8, 2020 (11 pages with English translation).

* cited by examiner

*Primary Examiner* — Suryaprabha Chunduru
(74) *Attorney, Agent, or Firm* — Eversheds Sutherland (US) LLP

(57) ABSTRACT

Disclosed are methods and kits for endonuclease-assisted DNA amplification reaction using decontaminated primer solutions that are pre-treated with a nuclease. Nucleic acid amplification assays that employ nuclease-resistant, inosine-containing primers, endonuclease V enzymes to introduce a nick into a target DNA comprising at least one inosine, and a DNA polymerase to generate amplicons of a target DNA are also disclosed.

9 Claims, 4 Drawing Sheets

Specification includes a Sequence Listing.

SEQUENCE LISTING

<160> NUMBER OF SEQ ID NOS: 40

<210> SEQ ID NO 1
<211> LENGTH: 225
<212> TYPE: PRT
<213> ORGANISM: Escherichia coli

<400> SEQUENCE: 1

```
Met Ile Met Asp Leu Ala Ser Leu Arg Ala Gln Gln Ile Glu Leu Ala
1               5                   10                  15

Ser Ser Val Ile Arg Glu Asp Arg Leu Asp Lys Asp Pro Pro Asp Leu
            20                  25                  30

Ile Ala Gly Ala Asp Val Gly Phe Glu Gln Gly Gly Glu Val Thr Arg
        35                  40                  45

Ala Ala Met Val Leu Leu Lys Tyr Pro Ser Leu Glu Leu Val Glu Tyr
    50                  55                  60

Lys Val Ala Arg Ile Ala Thr Thr Met Pro Tyr Ile Pro Gly Phe Leu
65                  70                  75                  80

Ser Phe Arg Glu Tyr Pro Ala Leu Leu Ala Ala Trp Glu Met Leu Ser
                85                  90                  95

Gln Lys Pro Asp Leu Val Phe Val Asp Gly His Gly Ile Ser His Pro
            100                 105                 110

Arg Arg Leu Gly Val Ala Ser His Phe Gly Leu Leu Val Asp Val Pro
        115                 120                 125

Thr Ile Gly Val Ala Lys Lys Arg Leu Cys Gly Lys Phe Glu Pro Leu
    130                 135                 140

Ser Ser Glu Pro Gly Ala Leu Ala Pro Leu Met Asp Lys Gly Glu Gln
145                 150                 155                 160

Leu Ala Trp Val Trp Arg Ser Lys Ala Arg Cys Asn Pro Leu Phe Ile
                165                 170                 175

Ala Thr Gly His Arg Val Ser Val Asp Ser Ala Leu Ala Trp Val Gln
            180                 185                 190

Arg Cys Met Lys Gly Tyr Arg Leu Pro Glu Pro Thr Arg Trp Ala Asp
        195                 200                 205

Ala Val Ala Ser Glu Arg Pro Ala Phe Val Arg Tyr Thr Ala Asn Gln
    210                 215                 220

Pro
225
```

<210> SEQ ID NO 2
<211> LENGTH: 227
<212> TYPE: PRT
<213> ORGANISM: Artificial Sequence
<220> FEATURE:
<223> OTHER INFORMATION: Mutant E. coli Endonuclease V

<400> SEQUENCE: 2

```
Met Ile Met Asp Leu Ala Ser Leu Arg Ala Gln Gln Ile Glu Leu Ala
1               5                   10                  15
```

```
Ser Ser Val Ile Arg Glu Asp Arg Leu Asp Lys Asp Pro Pro Asp Leu
         20                  25                  30

Ile Ala Gly Ala Asp Val Gly Phe Glu Gln Gly Gly Glu Val Thr Arg
         35                  40                  45

Ala Ala Met Val Leu Leu Lys Tyr Pro Ser Leu Glu Leu Val Glu Tyr
 50                      55                  60

Lys Val Ala Arg Ile Ala Thr Thr Met Pro Ala Ile Pro Gly Phe Leu
 65                  70                  75                  80

Ser Phe Arg Glu Tyr Pro Ala Leu Leu Ala Ala Trp Glu Met Leu Ser
                 85                  90                  95

Gln Lys Pro Asp Leu Val Phe Val Asp Gly His Gly Ile Ser His Pro
             100                 105                 110

Arg Arg Leu Gly Val Ala Ser His Phe Gly Leu Leu Val Asp Val Pro
         115                 120                 125

Thr Ile Gly Val Ala Lys Lys Arg Leu Cys Gly Lys Phe Glu Pro Leu
130                 135                 140

Ser Ser Glu Pro Gly Ala Leu Ala Pro Leu Met Asp Lys Gly Glu Gln
145                 150                 155                 160

Leu Ala Trp Val Trp Arg Ser Lys Ala Arg Cys Asn Pro Leu Phe Ile
                 165                 170                 175

Ala Thr Gly His Arg Val Ser Val Asp Ser Ala Leu Ala Trp Val Gln
             180                 185                 190

Arg Cys Met Lys Gly Tyr Arg Leu Pro Glu Pro Thr Arg Trp Ala Asp
         195                 200                 205

Ala Val Ala Ser Glu Arg Pro Ala Phe Val Arg Tyr Thr Ala Asn Gln
     210                 215                 220

Pro Leu Glu
225

<210> SEQ ID NO 3
<211> LENGTH: 221
<212> TYPE: PRT
<213> ORGANISM: Archaeoglobus fulgidus

<400> SEQUENCE: 3

Met Leu Gln Met Asn Leu Glu Glu Leu Arg Arg Ile Gln Glu Glu Met
1               5                   10                  15

Ser Arg Ser Val Val Leu Glu Asp Leu Ile Pro Leu Glu Glu Leu Glu
         20                  25                  30

Tyr Val Val Gly Val Asp Gln Ala Phe Ile Ser Asp Glu Val Val Ser
         35                  40                  45

Cys Ala Val Lys Leu Thr Phe Pro Glu Leu Glu Val Val Asp Lys Ala
 50                  55                  60

Val Arg Val Glu Lys Val Thr Phe Pro Tyr Ile Pro Thr Phe Leu Met
 65                  70                  75                  80

Phe Arg Glu Gly Glu Pro Ala Val Asn Ala Val Lys Gly Leu Val Asp
                 85                  90                  95

Asp Arg Ala Ala Ile Met Val Asp Gly Ser Gly Ile Ala His Pro Arg
            100                 105                 110

Arg Cys Gly Leu Ala Thr Tyr Ile Ala Leu Lys Leu Arg Lys Pro Thr
        115                 120                 125

Val Gly Ile Thr Lys Lys Arg Leu Phe Gly Glu Met Val Glu Val Glu
130                 135                 140

Asp Gly Leu Trp Arg Leu Leu Asp Gly Ser Glu Thr Ile Gly Tyr Ala
```

```
               145                 150                 155                 160
Leu Lys Ser Cys Arg Arg Cys Lys Pro Ile Phe Ile Ser Pro Gly Ser
                165                 170                 175
Tyr Ile Ser Pro Asp Ser Ala Leu Glu Leu Thr Arg Lys Cys Leu Lys
                180                 185                 190
Gly Tyr Lys Leu Pro Glu Pro Ile Arg Ile Ala Asp Lys Leu Thr Lys
                195                 200                 205
Glu Val Lys Arg Glu Leu Thr Pro Thr Ser Lys Leu Lys
                210                 215                 220

<210> SEQ ID NO 4
<211> LENGTH: 221
<212> TYPE: PRT
<213> ORGANISM: Artificial Sequence
<220> FEATURE:
<223> OTHER INFORMATION: Mutant Afu Endonuclease V

<400> SEQUENCE: 4

Met Leu Gln Met Asn Leu Glu Glu Leu Arg Arg Ile Gln Glu Glu Met
1               5                   10                  15
Ser Arg Ser Val Val Leu Glu Asp Leu Ile Pro Leu Glu Glu Leu Glu
                20                  25                  30
Tyr Val Val Gly Val Asp Gln Ala Phe Ile Ser Asp Glu Val Val Ser
            35                  40                  45
Cys Ala Val Lys Leu Thr Phe Pro Glu Leu Glu Val Asp Lys Ala
        50                  55                  60
Val Arg Val Glu Lys Val Thr Phe Pro Ala Ile Pro Thr Phe Leu Met
65                  70                  75                  80
Phe Arg Glu Gly Glu Pro Ala Val Asn Ala Val Lys Gly Leu Val Asp
                85                  90                  95
Asp Arg Ala Ala Ile Met Val Asp Gly Ser Gly Ile Ala His Pro Arg
                100                 105                 110
Arg Cys Gly Leu Ala Thr Tyr Ile Ala Leu Lys Leu Arg Lys Pro Thr
            115                 120                 125
Val Gly Ile Thr Lys Lys Arg Leu Phe Gly Glu Met Val Glu Val Glu
        130                 135                 140
Asp Gly Leu Trp Arg Leu Leu Asp Gly Ser Glu Thr Ile Gly Tyr Ala
145                 150                 155                 160
Leu Lys Ser Cys Arg Arg Cys Lys Pro Ile Phe Ile Ser Pro Gly Ser
                165                 170                 175
Tyr Ile Ser Pro Asp Ser Ala Leu Glu Leu Thr Arg Lys Cys Leu Lys
                180                 185                 190
Gly Tyr Lys Leu Pro Glu Pro Ile Arg Ile Ala Asp Lys Leu Thr Lys
                195                 200                 205
Glu Val Lys Arg Glu Leu Thr Pro Thr Ser Lys Leu Lys
                210                 215                 220

<210> SEQ ID NO 5
<211> LENGTH: 225
<212> TYPE: PRT
<213> ORGANISM: Termotoga maritima

<400> SEQUENCE: 5

Met Asp Tyr Arg Gln Leu His Arg Trp Asp Leu Pro Pro Glu Glu Ala
1               5                   10                  15
Ile Lys Val Gln Asn Glu Leu Arg Lys Lys Ile Lys Leu Thr Pro Tyr
                20                  25                  30
```

```
Glu Gly Glu Pro Glu Tyr Val Ala Gly Val Asp Leu Ser Phe Pro Gly
            35                  40                  45

Lys Glu Glu Gly Leu Ala Val Ile Val Val Leu Glu Tyr Pro Ser Phe
 50                  55                  60

Lys Ile Leu Glu Val Val Ser Glu Arg Gly Glu Ile Thr Phe Pro Tyr
 65                  70                  75                  80

Ile Pro Gly Leu Leu Ala Phe Arg Glu Gly Pro Leu Phe Leu Lys Ala
                 85                  90                  95

Trp Glu Lys Leu Arg Thr Lys Pro Asp Val Val Phe Asp Gly Gln
                100                 105                 110

Gly Leu Ala His Pro Arg Lys Leu Gly Ile Ala Ser His Met Gly Leu
                115                 120                 125

Phe Ile Glu Ile Pro Thr Ile Gly Val Ala Lys Ser Arg Leu Tyr Gly
            130                 135                 140

Thr Phe Lys Met Pro Glu Asp Lys Arg Cys Ser Trp Ser Tyr Leu Tyr
145                 150                 155                 160

Asp Gly Glu Glu Ile Ile Gly Cys Val Ile Arg Thr Lys Glu Gly Ser
                165                 170                 175

Ala Pro Ile Phe Val Ser Pro Gly His Leu Met Asp Val Glu Ser Ser
            180                 185                 190

Lys Arg Leu Ile Lys Ala Phe Thr Leu Pro Gly Arg Arg Ile Pro Glu
                195                 200                 205

Pro Thr Arg Leu Ala His Ile Tyr Thr Gln Arg Leu Lys Lys Gly Leu
            210                 215                 220

Phe
225

<210> SEQ ID NO 6
<211> LENGTH: 225
<212> TYPE: PRT
<213> ORGANISM: Artificial Sequence
<220> FEATURE:
<223> OTHER INFORMATION: Mutant Tma Endonuclease V

<400> SEQUENCE: 6

Met Asp Tyr Arg Gln Leu His Arg Trp Asp Leu Pro Pro Glu Glu Ala
 1               5                  10                  15

Ile Lys Val Gln Asn Glu Leu Arg Lys Lys Ile Lys Leu Thr Pro Tyr
                 20                  25                  30

Glu Gly Glu Pro Glu Tyr Val Ala Gly Val Asp Leu Ser Phe Pro Gly
            35                  40                  45

Lys Glu Glu Gly Leu Ala Val Ile Val Val Leu Glu Tyr Pro Ser Phe
 50                  55                  60

Lys Ile Leu Glu Val Val Ser Glu Arg Gly Glu Ile Thr Phe Pro Ala
 65                  70                  75                  80

Ile Pro Gly Leu Leu Ala Phe Arg Glu Gly Pro Leu Phe Leu Lys Ala
                 85                  90                  95

Trp Glu Lys Leu Arg Thr Lys Pro Asp Val Val Phe Asp Gly Gln
                100                 105                 110

Gly Leu Ala His Pro Arg Lys Leu Gly Ile Ala Ser His Met Gly Leu
                115                 120                 125

Phe Ile Glu Ile Pro Thr Ile Gly Val Ala Lys Ser Arg Leu Tyr Gly
            130                 135                 140

Thr Phe Lys Met Pro Glu Asp Lys Arg Cys Ser Trp Ser Tyr Leu Tyr
145                 150                 155                 160
```

```
Asp Gly Glu Glu Ile Ile Gly Cys Val Ile Arg Thr Lys Glu Gly Ser
            165                 170                 175

Ala Pro Ile Phe Val Ser Pro Gly His Leu Met Asp Val Glu Ser Ser
        180                 185                 190

Lys Arg Leu Ile Lys Ala Phe Thr Leu Pro Gly Arg Arg Ile Pro Glu
    195                 200                 205

Pro Thr Arg Leu Ala His Ile Tyr Thr Gln Arg Leu Lys Lys Gly Leu
210                 215                 220

Phe
225

<210> SEQ ID NO 7
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I

<400> SEQUENCE: 7
cccgcaaagt tcctcna                                              17

<210> SEQ ID NO 8
<211> LENGTH: 16
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (15)..(15)
<223> OTHER INFORMATION: I

<400> SEQUENCE: 8
accgggtctc cttcnc                                               16

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I

<400> SEQUENCE: 9
gctgcgcgaa ccacttna                                             18

<210> SEQ ID NO 10
<211> LENGTH: 15
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (14)..(14)
<223> OTHER INFORMATION: I

<400> SEQUENCE: 10
ccgtacccgg agcnc                                                15
```

```
<210> SEQ ID NO 11
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I

<400> SEQUENCE: 11
cagattcccg ccaganc                                                17

<210> SEQ ID NO 12
<211> LENGTH: 15
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (14)..(14)
<223> OTHER INFORMATION: I

<400> SEQUENCE: 12
ggcgaaccga tcanc                                                  15

<210> SEQ ID NO 13
<211> LENGTH: 14
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (13)..(13)
<223> OTHER INFORMATION: I

<400> SEQUENCE: 13
cggcggattc gcnc                                                   14

<210> SEQ ID NO 14
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I

<400> SEQUENCE: 14
ggttgacatc accccnc                                                17

<210> SEQ ID NO 15
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I

<400> SEQUENCE: 15
```

-continued gagcacctct tccagnc 17

<210> SEQ ID NO 16
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I

<400> SEQUENCE: 16
cgatcggaga cagctcnt 18

<210> SEQ ID NO 17
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: misc_feature
<222> LOCATION: (17)..(18)
<223> OTHER INFORMATION: Residues are linked via a phosphorothioate
      linkage
<220> FEATURE:
<221> NAME/KEY: modified_base
<222> LOCATION: (17)..(17)
<223> OTHER INFORMATION: I

<400> SEQUENCE: 17
acagccgcta gtcctant 18

<210> SEQ ID NO 18
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 18
cccgcaaagt tcctcna 17

<210> SEQ ID NO 19
<211> LENGTH: 16
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: misc_feature
<222> LOCATION: (15)..(16)
<223> OTHER INFORMATION: Residues are linked via a phosphorothioate
      linkage
<220> FEATURE:
<221> NAME/KEY: modified_base
<222> LOCATION: (15)..(15)
<223> OTHER INFORMATION: I

<400> SEQUENCE: 19
accgggtctc cttcnc                                            16

<210> SEQ ID NO 20
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 20
gctgcgcgaa ccacttna                                          18

<210> SEQ ID NO 21
<211> LENGTH: 15
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (14)..(15)
<223> OTHER INFORMATION: Residues are linked via a phosphorothioate
      linkage

<400> SEQUENCE: 21
ccgtacccgg agcnc                                             15

<210> SEQ ID NO 22
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 22
cagattcccg ccaganc                                           17

<210> SEQ ID NO 23
<211> LENGTH: 15
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (14)..(15)

```
<223> OTHER INFORMATION: Residues are linked via a phosphorothioate
      linkage

<400> SEQUENCE: 23
ggcgaaccga tcanc                                                    15

<210> SEQ ID NO 24
<211> LENGTH: 14
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (13)..(13)
<223> OTHER INFORMATION: I
<220> FEATURE:
<221> NAME/KEY: misc_feature
<222> LOCATION: (13)..(14)
<223> OTHER INFORMATION: Residues are linked via a phosphorothioate
      linkage

<400> SEQUENCE: 24
cggcggattc gcnc                                                     14

<210> SEQ ID NO 25
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 25
ggttgacatc accccnc                                                  17

<210> SEQ ID NO 26
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 26
gagcacctct tccagnc                                                  17

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
```

```
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 27
cgatcggaga cagctcnt                                                 18

<210> SEQ ID NO 28
<211> LENGTH: 16
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(16)
<223> OTHER INFORMATION: Residues are linked via a phosphorothioate
      linkage

<400> SEQUENCE: 28
gcctcgcctc ccgant                                                   16

<210> SEQ ID NO 29
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 29
ctgggattac aggcatnc                                                 18

<210> SEQ ID NO 30
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 30
ctcccgggtt caagcna                                                  17

<210> SEQ ID NO 31
<211> LENGTH: 18
<212> TYPE: DNA
```

```
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 31
gagatctcag ctcaccnc                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 32
caggctggag tgtaatng                                                 18

<210> SEQ ID NO 33
<211> LENGTH: 19
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(19)
<223> OTHER INFORMATION: Residues are linked via a phosphorothioate
      linkage

<400> SEQUENCE: 33
gacggagttt cactcttnt                                                19

<210> SEQ ID NO 34
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 34
ctgaggtcgg gagtttna                                                 18
```

<210> SEQ ID NO 35
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(17)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 35
gaggccaagg cgagtnn                                              17

<210> SEQ ID NO 36
<211> LENGTH: 17
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(17)
<223> OTHER INFORMATION: Residues are linked via a phosphorothioate
      linkage

<400> SEQUENCE: 36
ggcgcagtgg ctcacna                                              17

<210> SEQ ID NO 37
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate
      linkage

<400> SEQUENCE: 37
aaaatggggt aaggggnc                                             18

<210> SEQ ID NO 38
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(18)
<223> OTHER INFORMATION: Residues are linked via a phosphorothioate -continued

```
    linkage

<400> SEQUENCE: 38 accccgtca aactcant                                                       18

<210> SEQ ID NO 39
<211> LENGTH: 19
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(19)
<223> OTHER INFORMATION: Residues are linked via a phosphorothioate
    linkage

<400> SEQUENCE: 39
gtcatatact cagccctnc                                                     19

<210> SEQ ID NO 40
<211> LENGTH: 18
<212> TYPE: DNA
<213> ORGANISM: Artificial Sequence
<220> FEATURE:
<223> OTHER INFORMATION: Synthetic Primer Sequence
<220> FEATURE:
<221> NAME/KEY: modified_base
<222> LOCATION: (17)..(17)
<223> OTHER INFORMATION: I

<400> SEQUENCE: 40
acagccgcta gtcctant                                                      18
```

ENDONUCLASE-ASSISTED ISOTHERMAL AMPLIFICATION USING CONTAMINATION-FREE REAGENTS

CROSS REFERENCE TO RELATED APPLICATIONS

This application is a continuation of U.S. patent application Ser. No. 13/965,696, filed on Aug. 13, 2013 entitled "ENDONUCLEASE-ASSISTED ISOTHERMAL AMPLIFICATION USING CONTAMINATION-FREE REAGENTS", which is a continuation-in-part of U.S. patent application Ser. No. 13/330,745, filed on Dec. 20, 2011, which is a divisional of U.S. patent application Ser. No. 11/621,703, filed on Jan. 10, 2007, U.S. Pat. No. 8,202,972 B2, both entitled "ISOTHERMAL DNA AMPLIFICATION", all of which are incorporated in their entirety herein by reference.

SEQUENCE LISTING

The instant application contains a Sequence Listing which is submitted via EFS-Web and is hereby incorporated by reference in its entirety. Said ASCII copy, created on Nov. 9, 2018, is named 259103.5.v2.txt, and is 23,823 bytes in size.

FIELD OF INVENTION

The invention generally relates to nucleic acid synthesis methods and agents that employ at least one exonuclease-resistant, inosine-containing primer, at lease one endonuclease that is capable of introducing a nick in a double-stranded DNA sequence comprising an inosine residue at a residue 3' to the inosine residue, and at least one strand displacement DNA polymerase. It further relates to improved DNA amplification methods wherein the primer solution comprising the exonuclease-resistant, inosine-containing primer, which may further include reaction buffer and certain accessory protein(s) are pre-treated with an exonuclease to remove any contaminating nucleic acids before generating the DNA amplification reaction mixture.

BACKGROUND

DNA amplification is a process of copying a single or double-stranded target DNA to generate multiple copies of the target DNA. Since DNA strands are antiparallel and complementary, each strand may serve as a template (template strand) for the production of an opposite strand (complementary strand) by a DNA polymerase. The template strand is preserved as a whole or as a truncated portion and the complementary strand is assembled from nucleoside triphosphates. A variety of efficient nucleic acid amplification techniques are currently available such as polymerase chain reaction (PCR), ligase chain reaction (LCR), self-sustained sequence replication (3SR), nucleic acid sequence based amplification (NASBA), strand displacement amplification (SDA), multiple displacement amplification (MDA), or rolling circle amplification (RCA). Many of these techniques generate a large number of amplified products in a short span of time. For example, in a PCR, a target DNA, a pair of primers and a DNA polymerase are combined and subjected to repeated temperature changes that permit melting, annealing, and elongation steps to result in an exponential amplification of the starting target DNA.

DNA amplification often suffers from high background signals due to non-target or non-specific amplification reactions yielding undesired, false amplification products. For example, nucleic acid amplification reactions may get contaminated with unwanted nucleic acids (e.g., nucleic acids other than the target nucleic acid) in various ways yielding non-target amplification products. Contamination may arise from carry-over amplification products (amplicons) of previous amplification reactions, from the site from which the sample for amplification is collected, by exogenous DNA in the laboratory environment, or from reagents or reagent solutions used for amplification reaction. Non-specific amplification may result from various primer gymnastics such as nucleic acid template-independent primer-primer interactions. For example, primers may form primer-dimer structures by intra- or inter-strand primer annealing (via intra molecular or inter molecular hybridizations), and may get amplified, and may sometimes predominate, inhibit, or mask the amplification of a target DNA sequence. Such background amplification reactions become even more problematic where the target nucleic acid to be amplified is available only in limited quantities (e.g., whole-genome amplification from a single target DNA molecule). Due to higher amplification efficiencies of the DNA amplification techniques, even the slightest contamination of the reagents or reagent solutions employed in the amplification reactions with an undesired nucleic acid molecule may result in a huge amount of false or undesired amplification products. If such amplification technologies are used for diagnostic applications, they would likely result in a false-positive diagnosis.

Various pre-amplification sterilization procedures have been developed to minimize these non-target or non-specific amplification reactions. For example, deoxythymidine triphosphate (dTTP) is substituted by deoxyuridine triphosphate (dUTP) in PCR amplifications to make PCR products distinguishable from template DNA. Use of uracil-N-glycosylase enzyme (UNG) in a pre-amplification step cleaves the carry-over amplicons at the incorporated uracil residues. In amplification reactions using the same primers and the same target sequences, enzymatic removal of amplicons from previous similar amplification reactions has also been reported. These methods take advantage of the fact that the contaminant amplicon carries its primer sites at or near the ends of the molecule whereas virtually all other template DNA molecules not arising themselves from a previous PCR reaction, do not have their primer sites so located. Single strand-specific exonuclease has been used for amplicon de-contamination during SDA reaction wherein either (or both) the target nucleic acid or the amplicons are in single stranded form. In such methods, even though both the target and amplicons are attacked, due to the short length of amplicons (25-2,000 nucleotides) and their lack of secondary structures, the amplicons are preferentially cleaved. Selectively activatable enzymes such as micrococcal nuclease and of DNA-binding agents have also been employed to de-contaminate the reagent solution. Enzymatic, physical or chemical pre-treatment of the sample has also been employed to remove or inactivate a contaminating DNA that is originating from the site from where the sample is collected.

Apart from amplicon carry-over, reagents and reagent solutions, commonly used to amplify nucleic acids, may also contain unwanted nucleic acid contaminants that could potentially interfere with standard nucleic acid amplification protocols and procedures. Contaminating DNA may be much longer than that of a primer or an amplicon and specific information about the contaminating DNA may often be minimal. So, there exists a need to de-contaminate the reagents and the reagent solutions used for amplification reactions. As noted, the invention relates generally to the use of exonuclease-resistant, inosine-containing primers for endonuclease-assisted DNA amplification (referred as "Ping Pong" amplification) as well as the pre-amplification treatment of amplification solutions containing the exonuclease-resistant primers with an exonuclease to remove contaminating nucleic acids prior to the Ping-Pong amplification reaction.

BRIEF DESCRIPTION

In some embodiments, a nucleic acid amplification method is used that comprises the steps of providing a target DNA and a primer solution comprising at least one exonuclease-resistant, inosine-containing primer; generating a DNA amplification reaction mixture by mixing together the target DNA, the primer solution, at least one 5'→3' exonuclease-deficient DNA polymerase having strand displacement activity, and at least one endonuclease that is capable of nicking an inosine-containing strand of a double stranded DNA at a residue 3' to an inosine residue; and amplifying at least one portion of the target DNA using the DNA amplification reaction to produce at least one amplicon. Before generating the DNA amplification mixture, the primer solution, which may further include other nucleic acid amplification reagents (e.g., dNTPs, buffers, accessory proteins) may be decontaminated by treating with at least one exonuclease to remove any contaminating nucleic acid.

In some embodiments a method for producing at least one amplicon based on a target DNA is provided, wherein the method comprises the steps of (a) providing the target DNA; (b) providing a primer solution consisting essentially of an exonuclease-resistant, inosine-containing primer; (c) treating the primer solution with an exonuclease(s) to remove any contaminating nucleic acids from the primer solution; (d) inactivating the exonuclease(s) in the primer solution after the decontamination step (c); (e) generating a DNA amplification reaction mixture by mixing together the target DNA, the decontaminated primer solution, at least one 5'→3' exonuclease-deficient DNA polymerase having strand displacement activity, and at least one endonuclease that is capable of nicking a DNA at a residue 3' to an inosine residue; and (f) amplifying at least one portion of the target DNA using the DNA amplification reaction mixture of step (e) to produce the amplicon. The primer solution may further comprise other nucleic acid amplification reagents such as dNTPs, accessory protein(s), and amplification buffers.

An embodiment of kit comprises at least one exonuclease-resistant, inosine-containing primer, at least one 5'→3' exonuclease-deficient DNA polymerase having strand displacement activity, and at least one endonuclease that is capable of nicking an inosine-containing strand of a double stranded DNA at a residue 3' to the inosine residue.

DRAWINGS

These and other features, aspects and advantages of the present invention will become better understood when the following detailed description is read with reference to the accompanying figures.

DETAILED DESCRIPTION

Figure 1:
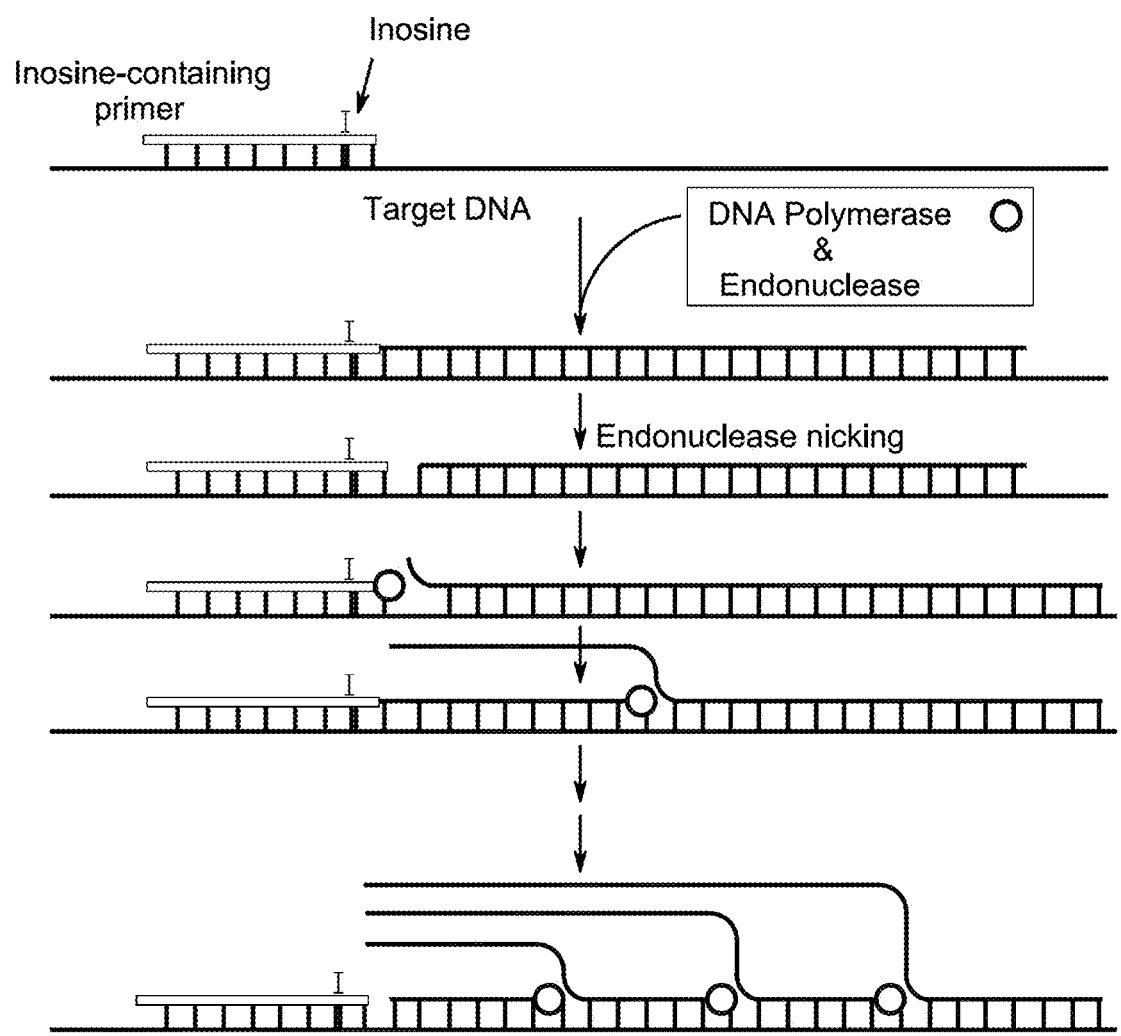
FIG. 1 illustrates a schematic representation of an embodiment of endonuclease-assisted nucleic acid amplification reaction.

To more clearly and concisely describe and point out the subject matter of the claimed invention, the following definitions are provided for specific terms, which are used in the following description and the appended claims.

As used herein, the term "target DNA" refers to a DNA sequence of either natural or synthetic origin that is desired to be amplified in a DNA amplification reaction. The target DNA acts as a template in the nucleic acid amplification reaction. In a DNA amplification reaction, either a portion of a target DNA or the entire region of a target DNA may get amplified by a DNA polymerase to produce one or more amplification products (amplicons). The target DNA may be obtained from a biological sample (i.e., a sample obtained from a biological subject) in vivo or in vitro. The target DNA may be obtained from, but are not limited to, body fluid (e.g., blood, blood plasma, serum, or urine), organs, tissues, fractions and sections (e.g., sectional portions of an organ or tissue) and cells isolated from a biological subject or from a particular region (e.g., a region containing diseased cells, or circulating tumor cells) of a biological subject. The biological sample that contains or suspected to contain the target DNA may be of eukaryotic origin, prokaryotic origin, viral origin or bacteriophage origin. For example, the target DNA may be obtained from an insect, a protozoa, a bird, a fish, a reptile, a mammal (e.g., rat, mouse, cow, dog, guinea pig, or rabbit), or a primate (e.g., chimpanzee or human). The target DNA may also be a cDNA (complementary DNA). The cDNA may be generated from an RNA template (e.g., mRNA, ribosomal RNA) using a reverse transcriptase enzyme. The DNA product generated by another reaction, such as a ligation reaction, a PCR reaction, or a synthetic DNA may also serve as the target DNA. The target DNA may be dispersed in solution or may be immobilized on a solid support, such as in blots, assays, arrays, glass slides, microtiter, on beads or ELISA plates.

As used herein, the term "contaminating nucleic acid" refers to an undesirable nucleic acid (e.g., a nucleic acid other than the target DNA), which may interfere in a target DNA amplification reaction or may compete with the target DNA in a DNA amplification reaction. The contaminating nucleic acid may be present in a reagent, a reagent solution, or an apparatus that is used for target DNA amplification. In other words, a contaminating nucleic acid is any nucleic acid, which is not intended to be amplified, further characterized, or present in an assay to be performed. The contaminating nucleic acid may a RNA or DNA. For example, a DNA that is present in a reagent or reagent solution that is used for performing a DNA synthesis reaction, prior to adding a target DNA to be amplified, is considered to be a contaminating nucleic acid. The contaminating nucleic acid may also be a prior amplicon from a previous amplification reaction. The contaminating nucleic acid in a DNA synthesis reaction may act as a potential DNA template or may act as a primer and thus may participate in the DNA synthesis reaction, resulting in unwanted amplification products. It is therefore desirable to remove any such contaminating nucleic acid prior to addition of the target DNA to the DNA amplification reaction mixture so that the contaminating nucleic acid will not interfere with the DNA amplification reaction. Prior removal of contaminating DNA from the reagents and/or reagent solutions is particularly desired to reduce artifacts during DNA synthesis reaction if the DNA template to be amplified is available only in limited amounts.

As used herein, the term "DNA amplification reaction mixture" refers to a mixture of reagents that is essential for performing a DNA amplification reaction. The DNA amplification reaction mixture disclosed herein includes, at the minimum, at least one exonuclease-resistant, inosine-containing primer, at least one target DNA, dNTPs, at least one endonuclease that is capable of nicking an inosine-containing strand of a double stranded DNA at a reside 3' to the inosine residue and at least one DNA polymerase having strand displacement activity. It may further include reagents such as buffer(s), salt(s) and other components (e.g., accessory proteins such as single stranded DNA binding protein, denaturant like urea, glycerol or pyrolidine) that are required for a typical DNA amplification reaction.

As used herein, the term "decontaminating" refers to altering or modifying a contaminating nucleic acid that may be present in a solution or a reaction mixture such that it cannot interfere or compete with the target DNA in a subsequent DNA amplification reaction. Decontamination may also refer to rendering a contaminating nucleic acid inert. The decontamination can be affected by chemical modification of a contaminating nucleic acid, for example, by removing of one or more functional groups so that the contaminating nucleic acid is unable to react with a DNA template (for it to act as a primer) or a DNA polymerase (for it to act as a DNA template). The contaminating nucleic acid may also be rendered inert by degrading or digesting the nucleic acid. Depending on the nature of the reagents employed, the mechanism by which the nucleic acid is rendered inert may vary. For example, a contaminating nucleic acid may be rendered inert by digesting the contaminating nucleic acid with an exonuclease to produce free nucleotides having a 3'-hydroxyl group and a 5'-phosphate group. The decontamination may result either in a reduction in the amount of the contaminating nucleic acid or a complete removal of the contaminating nucleic acid. The decontamination process often leads to nucleotides or nucleotide fragments, which cannot act as a primer or serve as a template for a subsequent DNA amplification reaction.

As used herein, the term "primer" refers to a short linear oligonucleotide that hybridizes to a target nucleic acid sequence (e.g. a target DNA) to prime a nucleic acid synthesis reaction. The primer may be an RNA oligonucleotide, a DNA oligonucleotide, or a chimeric sequence. The primer may contain natural, synthetic, or modified nucleotides. For example, the primer may comprise naturally occurring nucleotides (G, A, C or T nucleotides) or their analogues. Both the upper and lower limits of the length of the primer sequence are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acids under such hybridization conditions. The upper limit is often determined by the possibility of having a duplex formation in a region other than the pre-determined nucleic acid sequence in the target nucleic acid. Generally, suitable primer lengths are in the range of about 4 nucleotides long to about 40 nucleotides long. In some embodiments the primer ranges in length from 5 nucleotides to 30 nucleotides. The term "forward primer" refers to a primer that anneals to a first strand of the target DNA and the term "reverse primer" refers to a primer that anneals to a complimentary, second strand of the target DNA. Together, a forward primer and a reverse primer are generally oriented on the target DNA sequence in a manner analogous to PCR primers, such that a DNA polymerase can initiate the DNA synthesis resulting in replication of both strands.

As used herein, the term "inosine-containing primer" refers to a primer comprising at least one inosine residue in its sequence. The inosine residue is a 2'-deoxyribonucleoside or 2'-ribonucleoside residue wherein the nucleobase is a hypoxanthine. The inosine residue is capable of base pairing with a thymine, an adenine, a cytidine or a uridine residue. The inosine residue may also be an inosine analogue. For example, xanthine structures are alternate structures to inosine residues, resulting from deamination of guanine. Inosine analog refers to a 2'-deoxyribonucleoside or 2'-ribonucleoside wherein the nucleobase includes a modified base such as xanthine, uridine, oxanine (oxanosine), other 0-1 purine analogs, N-6-hydroxylaminopurine, nebularine, 7-deaza hypoxanthine, other 7-deazapurines, and 2-methyl purines. The inosine or inosine analogue residue may be positioned near the 3' terminal end of a primer sequence, often as a penultimate nucleotide at the 3' end of the primer sequence.

As used herein, the term "exonuclease resistant, inosine-containing primer" refers to a primer sequence that contains at least one inosine residue and is also resistant to the action of an exonuclease enzyme (i.e., not degraded by the exonuclease). In some embodiments, the primer is resistant to both 3'→5' exonuclease activity and 5'→3' exonuclease activity. In some embodiments, the primer is resistant to 5'→3' exonuclease activity. The inosine-containing primer may be engineered to make it exonuclease-resistant by chemical modification, for example, by introduction of at least one phosphorothioate linkage at an appropriate position. For example, an inosine-containing primer that contains a phosphorothioate linkage between the 3' terminal nucleotide and the penultimate residue is resistant to the action of exonuclease in a 3'→5' direction. Since the 3'→5' exonuclease digests the nucleic acid in a 3' to 5' direction, the phosphorothioate linkage at this position prevents the digestive action of the exonuclease. If the inosine residue is present on the 5' side of the phosphorothioate, it will be maintained in the primer. Similarly, an inosine-containing primer that contains a phosphorothioate linkage between the 5' terminal nucleotide and the penultimate residue is resistant to the action of exonuclease in a 5'→3' direction. When exonuclease-resistant, inosine containing primer hybridizes with a target DNA and forms double stranded nucleic acid structure, the double stranded structure may be recognized by specific endonucleases resulting in a single stranded nick in the inosine-containing strand. For example, endonuclease V is capable of nicking the inosine-containing strand of a double stranded DNA at a position 3' to the inosine residue when the exonuclease-resistant inosine-containing primer is hybridized to a target DNA.

As used herein, the term "dNTPs" refers to a mixture of deoxynucleotide triphosphates that act as precursors required by a DNA polymerase for DNA synthesis. Each of the deoxynucleotide triphosphates in a dNTP mixture comprises a deoxyribose sugar, an organic base, and a phosphate in a triphosphate form. A dNTP mixture may include each of the naturally occurring deoxynucleotide triphosphate (e.g., dATP, dTTP, dGTP, dCTP or dUTP). In some embodiments, each of the naturally occurring deoxynucleotide triphosphates may be replaced or supplemented with a synthetic analog; provided however that inosine base may not replace or supplement guanosine base (G) in a dNTP mixture. Each of the deoxynucleotide triphosphates in dNTP may be present in the reaction mixture at a final concentration of 10 µM to 20,000 µM, 100 µM to 1000 µM, or 200 µM to 300 µM.

As used herein, the term "amplicon" refers to nucleic acid amplification products that result from the amplification of a target nucleic acid. Amplicons may comprise a mixture of amplification products (e.g. a mixed amplicon population), several dominant species of amplification products (e.g. multiple, discrete amplicons), or a single dominant species of amplification product. A single species of amplicon may be isolated from a mixed population of amplicons using art-recognized techniques, such as affinity purification or electrophoresis. An amplicon may comprise single-stranded or double-stranded DNA, DNA:RNA hybrids or RNA depending on the reaction scheme used. An amplicon may be largely single-stranded or partially double-stranded or completely double-stranded DNA, DNA:RNA hybrids, or RNA.

As used herein, the term "terminal nucleotide" refers to a nucleotide that is located at a terminal position of an oligonucleotide or primer sequence. The terminal nucleotide that is located at a 3' terminal position of an oligonucleotide sequence is referred as a 3' terminal nucleotide, and the terminal nucleotide that is located at a 5' terminal position is referred as a 5' terminal nucleotide. The nucleotide that is located at a penultimate position refers to a nucleotide that is immediately adjacent to a terminal nucleotide. For example, NNNNNNIA depicts a nucleotide sequence (an octamer) in which the inosine residue (I) is at a penultimate 3' position and an adenosine residue is the 3' terminal nucleotide.

The term "mutant endonuclease" or "engineered endonuclease" as used herein refers to an endonuclease enzyme that is generated by genetic engineering or protein engineering, wherein one or more amino acid residues are altered from the wild type endonuclease. The alteration may include a substitution, a deletion or an insertion of one or more amino acid residues. Throughout the specification and claims, the substitution of an amino acid at one particular location in the protein sequence is referred using a notation "(amino acid residue in wild type enzyme) (location of the amino acid in wild type enzyme) (amino acid residue in engineered enzyme)". For example, a notation Y75A refers to a substitution of a Tyrosine (Y) residue at the $75^{th}$ position of the wild type enzyme by an Alanine (A) residue (in mutant/engineered enzyme).

The term "conservative variants", as used herein, applies to both amino acid and nucleic acid sequences. With respect to particular nucleic acid sequences, the term "conservative variants" refers to those nucleic acids that encode identical or similar amino acid sequences (i.e., amino acid sequences that have similar physico-chemical properties) and include degenerate sequences. For example, the codons GCA, GCC, GCG, and GCU all encode alanine. Thus, at every amino acid position where an alanine is specified, any of these codons may be used interchangeably in constructing a corresponding nucleotide sequence. Such nucleic acid variants are conservative variants, since they encode the same protein (assuming that is the only alternation in the sequence). One skilled in the art recognizes that each codon in a nucleic acid, except for AUG (sole codon for methionine) and UGG (tryptophan) may be modified conservatively to yield a functionally identical peptide or protein molecule. As to amino acid sequences, one skilled in the art will recognize that alteration of a polypeptide or protein sequence via substitutions, deletions, or additions of a single amino acid or a small number (typically less than about ten) of amino acids may be a "conservative variant" if the physico-chemical properties of the altered polypeptide or protein sequence is similar to the original. In some cases, the alteration may be a substitution of one amino acid with a chemically similar amino acid. Examples of conservative variants include, but not limited to, the substitution of one hydrophobic residue (e.g., isoleucine, valine, leucine or methionine) for one another; or the substitution of one polar residue for another (e.g., the substitution of arginine for lysine, glutamic for aspartic acid, or glutamine for asparagine) and the like. Genetically encoded amino acids generally may be divided into four families: (1) acidic: aspartate, glutamate; (2) basic: lysine, arginine, histidine; (3) nonpolar: alanine, valine, leucine, isoleucine, proline, phenylalanine, methionine, tryptophan; and (4) uncharged polar: glycine, asparagine, glutamine, cysteine, serine, threonine, tyrosine.

One or more embodiments of the methods and kits for endonuclease-assisted DNA amplification assays comprises use of an endonuclease that is capable of nicking an inosine-containing strand of a double-stranded nucleic acid at a location 3' to the inosine residue. In some embodiments, the endonuclease is a genetically engineered endonuclease. The DNA amplification assays described herein further employ an exonuclease-resistant primer that comprises at least one inosine residue. The exonuclease-resistant primer solution may be decontaminated prior to the DNA amplification reaction by treating it with an appropriate exonuclease.

For DNA amplification assays, samples suspected or known to contain a particular target DNA may be obtained from a variety of sources. The sample may be, for example, a biological sample, a food, an agricultural sample, or an environmental sample. Samples may also be derived from a variety of biological subjects, including prokaryotic or eukaryotic origin and includes viruses. The sample may be derived from a biological tissue or a body fluid or an exudate (e.g., blood, plasma, serum or urine, milk, cerebrospinal fluid, pleural fluid, lymph, tears, sputum, saliva, stool, lung aspirates, throat or genital swabs, and the like), whole cells, circulating tumor cells, cell fractions, or cultures.

The target DNA for a nucleic acid assay may be dispersed in solution or immobilized on a solid support (such as blots, paper punches, arrays, microtiter, or well plates). The target DNA may either be single-stranded or double-stranded. The target DNA template can be a circular DNA, a linear DNA or a nicked DNA. The DNA template may be a genomic DNA, a plasmid DNA or a cDNA. The target DNA may be pretreated to make it available for hybridization with the primer. For example, when a target DNA is in a double stranded form, it may be denatured to generate a single stranded form of the target DNA. The target double stranded DNA may be thermally or chemically denatured, or both thermally and chemically denatured. In some embodiments, the double stranded DNA is chemically denatured using a denaturant (e.g., glycerol, ethylene glycol, formamide, or a combination thereof) that reduces the melting temperature of double stranded DNA. In certain embodiments, the denaturant reduces the melting temperature by 3° C. to 6° C. for every 10% (vol./vol.) of the denaturant added to the reaction mixture. The denaturant or combination of denaturants may comprise 1%, 5%, 10% (vol./vol.), 15% (vol./vol.), 20% (vol./vol.), or 25% (vol./vol.) of reaction mixture. In certain embodiments, the denaturant comprises ethylene glycol. In alternative embodiments, the denaturant is a combination of glycerol (e.g., 10%) and ethylene glycol (e.g., 15% to 20%). Salts that reduce hybridization stringency may be included in the reaction buffers at low concentrations to chemically denature the target DNA is at low temperatures. In embodiments where the target DNA is thermally denatured the denaturing step comprises thermally denaturing the target DNA (e.g., by heating the target DNA at 95° C.).

In some embodiments, an endonuclease-assisted DNA amplification method produces at least one amplicon based on a target DNA. The target DNA is first hybridized with an exonuclease-resistant, inosine-containing primer followed by amplification of the target DNA using a DNA polymerase (e.g., a strand displacement polymerase) and dNTPs in presence of an endonuclease that is capable of nicking an inosine-containing strand of a double-stranded nucleic acid at a location 3' to the inosine residue. The dNTPs provide a combination of deoxyribonucleotides required by the DNA polymerase for DNA synthesis. DNA polymerases use dNTP mixture to add nucleotides to the 3' hydroxyl end of a primer annealed to a template strand of DNA in a complementary fashion, creating a new DNA strand (amplicon) complementary to the target DNA template. In some embodiments, each of the naturally occurring deoxynucleotides may be replaced or supplemented with a synthetic analog; provided however that deoxyinosinetriphosphate (dITP) may not replace or supplement dGTP in the dNTP mixture. The product of DNA amplification reaction may be single stranded or double-stranded DNA, often extending to the end of the template strand. The inosine nucleotide in the inosine-containing primer may be positioned at least 4 nucleotides, at least 5 nucleotides, or at least 10 nucleotides downstream of the 5' end of the inosine-containing primer. For example, the inosine containing random octamer primer may have a sequence such as NNNINNNN or NNNNINN. In certain embodiments, the inosine nucleotide may be the penultimate 3' nucleotide of the primer. In alternative embodiments, inosine may be present at both the penultimate 3' residue and ultimate 3' residue. In some embodiments, the inosine-containing primer comprises an inosine analogue. In some embodiments, the DNA amplification method comprises the steps of providing a target DNA and a primer solution comprising at least one exonuclease-resistant, inosine-containing primer; generating a DNA amplification reaction mixture by mixing together the target DNA, the primer solution, at least one 5'→3' exonuclease-deficient DNA polymerase having strand displacement activity, and at least one endonuclease that is capable of nicking an inosine-containing strand of a double stranded DNA at a residue 3' to an inosine residue; and amplifying at least one portion of the target DNA using the DNA amplification reaction to produce at least one amplicon. The at least one exonuclease-resistant, inosine-containing primer may be a forward primer or a reverse primer or a mixture of both. Apart from the exonuclease-resistant, inosine-containing primer, the primer solution may include other essential nucleic acid amplification reagents such as dNTPs and buffers. The primer solution may also include one or more of reagents that enhance or assist DNA amplification reaction such as single strand DNA binding protein (SSB protein), formamide, ethylene glycol, or Ficoll. Before generating the DNA amplification mixture, the primer solution, may be decontaminated by treating the primer solution with an appropriate exonuclease to remove any contaminating nucleic acid. Further, after the decontamination reaction, the added exonuclease may be inactivated prior to the DNA amplification reaction. In some embodiments, the target DNA is amplified by employing an isothermal amplification method.

FIG. 1 depicts a schematic representation of an embodiment of endonuclease-assisted target DNA amplification. Upon binding of an inosine-containing primer to the target DNA, the DNA polymerase (e.g., a 5'→3' exonuclease-deficient Bst DNA polymerase) extends the inosine-containing primer thereby generating a double stranded DNA (primer extension product). The extension reaction creates a nicking site for an endonuclease, which is capable of creating a single stranded nick at the inosine-containing strand of a double stranded DNA at a position 3' to the inosine residue. The endonuclease nicks the double stranded DNA at this nicking site. Nicking creates a new DNA synthesis initiation site for the DNA polymerase. The DNA polymerase binds to this initiation site and further elongates the nicked primer. Since the DNA polymerase has strand displacement activity, it displaces a single-stranded DNA product while it re-creates the double-stranded primer extension product. This cycle repeats, synthesizing multiple single strands of DNA complementary to the downstream portion of the target DNA template. The schematic representation of a nucleic acid amplification shown in FIG. 1 may be varied by employing additional primers or other oligonucleotides, additional enzymes, additional nucleotides, stains, dyes, or other labeled components. For example, amplification with a single primer may be used for dideoxy sequencing, producing multiple sequencing products for each molecule of template, and, optionally by the addition of dye-labeled dideoxynucleotide terminators. Labeled probes may be generated from double-stranded cDNA made with a sequence-tagged oligo dT primer from mRNA samples. A single primer may be the complement of the tag sequence, facilitating identification and/or isolation. An endonuclease V may be used as a suitable endonuclease for this reaction. Endonuclease V is a repair enzyme that recognizes DNA containing inosines (or inosine analogues) and hydrolyzes the second or third phosphodiester bonds 3' to the inosine (i.e., specifically nicks a DNA at a position two nucleotides 3' to an inosine nucleotide, about 95% the second phosphodiester bond and about 5% the third phosphodiester bond) leaving a nick with 3'-hydroxyl and 5'-phosphate. When the target DNA is double stranded the nick occurs in the strand comprising the inosine residue.

In some embodiments, a strand displacement DNA polymerase, an endonuclease V and an exonuclease-resistant, inosine-containing primer are employed in the DNA amplification reaction. For DNA amplification, the exonuclease-resistant, inosine-containing primer hybridizes with the target DNA. Inosine residue in the primer may base pair with a cytidine residue or a thymidine residue in the target DNA, wherein hypoxanthene substitutes for a guanine to complement a cytosine; or substitutes for an adenine to complement a thymine. A complimentary strand to the target DNA template is then generated by DNA synthesis thereby generating a double-stranded DNA. Generation of the double stranded DNA in turn generates a nicking site for the endonuclease V. The endonuclease V nicks the inosine-containing strand of this double-stranded DNA. The DNA polymerase then once again generates the complementary strand from the nicked position. This elongation step once again creates a nicking site for the endonuclease V. Thus the elongation by the DNA polymerase followed by nicking by the endonuclease V gets repeated multiple times until any one of the essential DNA amplification reagents in the DNA amplification reaction mixture is exhausted. In each cycle, the strand displacement DNA polymerase employed in these reactions displaces the complementary strand that was generated in the previous cycle. The steps of hybridization, elongation, nicking and further elongation may occur substantially simultaneously. Thus, one or more embodiments of the methods comprise an inosine residue that is introduced into a specific position of a target nucleic acid (via an oligonucleotide primer), followed by repeated generation of complimentary strand of the target nucleic acid using a polymerase and an endonuclease V that nicks the generated double stranded nucleic acid at the inosine-containing strand to initiate a second cycle of complementary strand generation by the polymerase.

Figure 2:
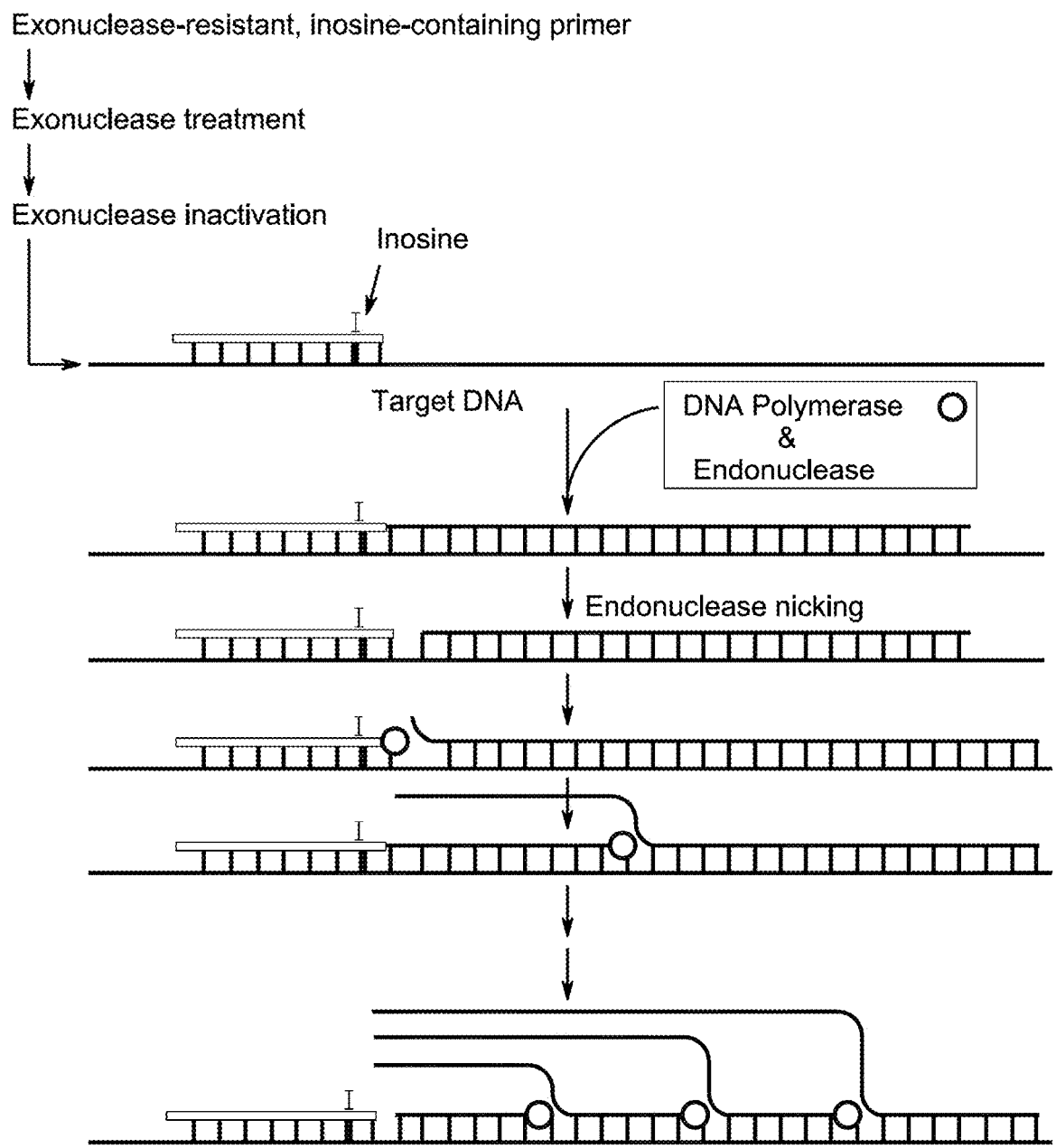
FIG. 2 illustrates a schematic representation of an embodiment of endonuclease-assisted nucleic acid amplification reaction using an exonuclease-resistant, inosine-containing primer.

FIG. 2 depicts a schematic representation of an embodiment of the endonuclease-assisted amplification reaction using exonuclease-resistant, inosine-containing primer. The sequence of the exonuclease-resistant, inosine-containing primers used in the amplification reaction typically depends on the sequence of the DNA template to be amplified and/or the desired type of amplification (e.g., random vs. specific). In some embodiments, the exonuclease-resistant, inosine-containing primer used herein comprises at least one inosine residue located at least 4 nucleotides downstream of the 5' terminal residue. The exonuclease-resistant primers may include modified nucleotides, which make them resistant to the exonuclease digestion. In some embodiments, the primer contains at least one nucleotide that makes the primer resistant to degradation by an exonuclease, particularly by a 3'→5' exonuclease. The modified nucleotide may be a phosphorothioate nucleotide. For example, an exonuclease resistant primer may possess one, two, three or four phosphorothioate linkages between nucleotides in the sequence (e.g., NNNNN*N*N*I*N or N*NNNN*N*N*I*N). The modified nucleotide is commonly a 3'-terminal nucleotide of the primer sequence having a penultimate inosine residue (e.g., (NNN)$_n$NI*N or (NNN)$_n$NI*I where * represents a phosphorothioate bond between the nucleotides and the integer value of n may range depending on the length of the primer used, for example, the value of n may range from 0 to 13). However in some embodiments the primer could have the modified nucleotide as the inosine residue (e.g., NNNNNN*IN). In some embodiments, the modified nucleotide may be located at a position other than the 3'-terminal position provided that the primer sequence contains at least one inosine residue located next to the modified residue (e.g., NNNNI*NNNN or NNNN*INNNN). When the modified nucleotide is located at positions other than the 3'-terminal end of a primer sequence, the 3'-terminal nucleotide of said primer may be removed by the 3'→5' exonuclease activity. Some endonuclease V may have an associated 3'→5' exonuclease activity. The thioated inosine primers may prevent the endonuclease V from removing the inosine. Other nucleotide modifications known in the art that make a nucleotide sequence resistant to an exonuclease may be used as well.

Suitable inosine-containing primers that are also exonuclease-resistant may be designed and selected depending on the sequence and the nature of the DNA template to be amplified. Exonuclease-resistant, inosine-containing primers may be synthesized using any of the art-recognized synthesis techniques. Amplicons may be generated using a single inosine-containing primer, paired inosine-containing primers, or nested-paired inosine-containing primers that are exonuclease resistant. Primer design software such as Auto-Dimer™ may be employed to design a single primer or multiple primers that are capable of annealing to a nucleic acid and facilitating polymerase extension. The exonuclease-resistant, inosine-containing primer may be designed in such a way that the melting temperature of the primer is about 50° C. with a salt concentration of about 6 mM. In some embodiments, relatively short primers (e.g., 10-mers to 20-mers; more preferably 14-mers to 18-mers, most preferably 16-mers) may be employed. The exonuclease-resistant, inosine-containing primer may either be a specific primer or a random primer. For whole genome amplification reaction, a random primer mixture comprising primers generated by randomizing all the residues other than the inosine residue may be used. Either a single primer or multiple primers may be employed for amplification. Specific primers have, or are engineered to have, a nucleotide sequence that is complementary, in the Watson-Crick sense, to a pre-determined sequence, which is present in the target DNA template.

In some embodiments, the exonuclease-resistant, inosine-containing primer is designed such that the inosine residue is positioned in the primer at a location complementary to a cytosine residue in the target DNA. In some embodiments, the inosine appears as the penultimate 3' base of the primer. Because the reaction conditions (e.g., temperature and ionic strength) affect annealing of primer to target DNA, optimal positioning of the inosine in the primer may be adjusted according to the reaction conditions. In general, the inosine residue is positioned away from the 5' end of the prime such that the primer remains annealed to the target DNA after nicking by the endonuclease (e.g., the length of the nicked primer is sufficient to enable binding to the target DNA under the nucleic acid assay reaction conditions). Accordingly, the segment of the primer 5' of the inosine should have a melting temperature approximately equal to the reaction temperature at the chosen reaction conditions. In some embodiment, the inosine-containing primer may comprise more than one inosine residue or inosine analogues. If there are two template Gs in a row, two inosines may appear in the primer as the both the penultimate 3' and the final residues. In this case, nicking by the endonuclease 2 nucleotides 3' to either inosine residues would have the same effect of creating a nicked DNA strand. The inosine residues may be located both at the penultimate 3' position and the terminal 3 position. These two inosines may be linked by phosphorothioate linkages. In some embodiments, the inosine-containing primer may demonstrate a melting temperature of 25° C. to 80° C., 30° C. to 65° C., or 40° C. to 55° C. in the reaction mixture. In some embodiments, the exonuclease-resistant, inosine-containing primer demonstrates a melting temperature of 50° C. in the reaction mixture.

With a single, forward primer, the rate of synthesis of complimentary copies of target DNA is relatively constant, resulting in a steady, linear increase in the number of complimentary copies with time. Multiple primers, each of them containing at least one inosine residue and are exonuclease-resistant, may be included in the reaction mixture in some embodiments to accelerate the amplification process. Embodiments where both the plus and minus strands are generated, paired primers comprising a forward primer and a reverse primer may be included in the reaction mixture. For example, when a reverse primer (a primer that anneals to the generated complementary strand ((+) strand) to further generate a (−) strand in the reverse direction) that anneals to the complementary strand of target DNA at a defined distance from the forward primer is added, the amplification process is accelerated. Since the targets for each of these primers would be present in the original template, both strands would be amplified in the two primer scheme ("Ping product" being the amplicon of the forward primer and the "Pong product" being the amplicon of the reverse primer). The inclusion of multiple paired primers may improve the relative percentage of a discrete product in the reaction mixture. The internal most forward and internal most reverse primers may be placed relatively close to each other (e.g., less than about 50 bases apart), minimizing the time required to complete the forward amplicon ((+) strand) to its 5' end as defined by the endonuclease V cleavage site, and thereby reducing the total time required to generate amplicons from the target DNA. The reaction rate reaches a maximum when the amount of nuclease, polymerase, or any other component(s) becomes limiting. Additional pairs of nested primers, each of them exonuclease-resistant and containing at least one inosine residue, may also be used to further increase amplification rates or increase the specificity of the reaction. Nested primers may be designed to bind at or near the 3' end of the previous amplicon so that in a series, each primer in the series will hybridize next to each other on the original target. Where multiple nested primers are used, SSB protein at a concentration of 1 ng to 10 μg in a 10 μL volume may be included in the reaction mixture to increase fidelity and to reduce background. Amplification with multiple, paired primers facilitates rapid and extensive amplification, which is useful to detect the presence of specific sequences, to quantify the amounts of those sequences present in a sample, or to produce quantities of a sequence for analysis by methods such as electrophoresis for size measurement, restriction enzyme digestion, sequencing, hybridization, or other molecular biological techniques.

In some embodiments, extender templates, which are specific primer sequences (e.g., primers that contain additional 5' sequences that allow for additional sequence to be added to the end of hybridized amplicon DNA, and are used to generate a promoter sequence or a restriction endonuclease site specific sequence or a novel primer binding site sequence), may be annealed at the 3' end of the amplicon by incorporating in an exonuclease-resistant, inosine-containing primer. An extender template may be designed such that it anneals to the 3' end of an amplicon. If the extender template contains two stretches of sequences, one complementary to the amplicon, and one that is not, hybridization will create a 5' overhang of the non-complementary primer sequence. The 3' recessed end of the amplicon can then be further extended by the DNA polymerase. This extension reaction may be employed to incorporate specific DNA sequences at the 3' end of an amplicon. In some embodiments, the 5' end of the extender template may contain a hairpin loop, with a fluorescent dye and a quencher located on either arm of the stem such that the dye fluorescence is largely quenched by resonance energy transfer. Upon extension of the recessed 3' end of the amplicon by a DNA polymerase, the stem-loop structure gets converted to a double stranded structure and causes the dye and the quencher to be separated further. This eliminates some or all of the fluorescence quenching, and thus generates a detectable signal. This signal may be multiplexed by appropriate sequence selection of the extender templates and the color of the quenched dyes so that 2 or more independent amplification processes may be monitored simultaneously. In some embodiments the 5' end of the extender template may include the complement of an RNA polymerase promoter sequence. Thus, a double stranded RNA polymerase promoter may be generated by hybridizing the extender template to the amplicon followed by extension of the recessed 3' end of the amplicon by the DNA polymerase. If an RNA polymerase is included in the reaction, the amplicon may be then transcribed as a single-stranded RNA polymerase template to generate corresponding RNAs.

Since the exonuclease-resistant, inosine-containing primer is resistant to the action of exonuclease, the solution containing the primer can be pre-treated with an exonuclease before adding to the DNA amplification reaction mixture. The exonuclease treatment removes or reduces any contaminating nucleic acid that may be present in the primer solution. The solution containing the exonuclease-resistant, inosine-containing primer may further comprise other reagents required for a DNA amplification reaction described herein (except the target DNA) such as dNTPs, DNA polymerase, endonuclease, buffers and/or single strand-binding proteins. If DNA polymerase is included in the primer solution, it should be selected such that it can withstand the exonuclease inactivation step. Further, if a proofreading DNA polymerase such as Phi29 DNA polymerase is used as an exonuclease in the decontamination step, primer solution should not contain any dNTPs. The decontamination of the primer solution if often achieved by incubating the primer solution with an exonuclease and a divalent cation to allow the exonuclease to render the contaminating nucleic acid inert. A single exonuclease or a combination of exonucleases may be used to decontaminate the primer solution. In some embodiments, one or more of exonuclease may be used in the reaction. Suitable exonucleases that may be used in the present invention include, but not limited, to Phi29 DNA polymerase, exonuclease I, exonuclease III, exonuclease VII, T7 gene-6 exonuclease, spleen exonuclease, T5 D15 exonuclease and lambda exonuclease. In one embodiment, a combination of exonuclease I and exonuclease III is used in the decontaminating the primer solution. When Phi29DNA polymerase is used as the suitable exonuclease, it may be inactivated very easily by incubating the primer solution at 45 degrees, so the Phi29 DNA polymerase is inactive at the temperature used for DNA amplification.

Any divalent cation that can activate the exonuclease can be used in the decontamination reaction. Some non-limiting examples include magnesium and manganese. The concentration of the divalent cation primarily depends on the concentration of the exonuclease. Some of the parameters that determine the concentration of the exonuclease include the amount of contaminating nucleic acid, the turn-over of the particular exonuclease and other kinetic parameters for the exonuclease activity. In some embodiments, a molar excess of the divalent cation with respect to the exnuclease is used for decontaminating the primer solution. The primer solution containing the exonuclease-resistant, inosine-containing primer is incubated with the exonuclease and the divalent cation for a period of time that is sufficient to render the contaminating nucleic acid inert. The incubation time may vary with the kinetic properties of the exonuclease and the divalent cation that is being used. The incubation time may also depend on the temperature at which the incubation is performed. Incubation time may be optimized by analyzing the efficiency of the de-contamination process by employing any of the techniques known in the art for characterizing the presence of nucleic acids. Suitable incubation times may range from about 5 min. to about 3 h. In some embodiments, the incubation time may range from about 1 min to about 100 min. In some specific embodiments, the primer solution containing the exonuclease-resistant, inosine-containing primer may be incubated with the exonuclease and the divalent cation at 37° C. for about 60 min. The temperature at which the incubation of the primer solution is performed may vary by the nature of the particular exonuclease used. The maximum temperature that may be used for the incubation is limited by the stability of the exonuclease and the minimum temperature that may be employed for the incubation is decided by the exonuclease activity at that temperature. In some embodiments, the incubation is performed at a temperature at or below 50° C. In some embodiments, the suitable incubation temperature ranges from about 0° C. to about 45° C. In some specific embodiments, the incubation may be performed at a temperature between about 10° C. to about 40° C.

In some embodiment, a suitable endonuclease may be added to the primer solution along with the exonuclease for decontamination. This is particularly useful in embodiments wherein the contaminating nucleic acid may include a circular DNA or wherein the entire backbone of the primer is nuclease resistant. Endonucleases act on circular DNA and nick them. Once the nick is made, the exonuclease can act on the contaminant, nicked DNA and degrade them to make them inert. Non-limiting examples of suitable endonucleases include DNAses such as DNAse I.

In some embodiments, a SSB protein may be added along with the exonuclease to the primer solution containing exonuclease-resistant, inosine containing primer. Suitable SSB proteins that may include, but not limited to, extreme thermostable single stranded DNA-binding protein (ET SSB from New England Biolabs, MA), rec A (e.g., *E. coli* RecA), Tth RecA (RecA homolog isolated from *Thermus thermophilus* from New England Biolabs, MA), phage T4 gene-32 protein, T7 gene 2.5 protein, Ncp7, and *E. coli* SSB protein. The addition of exonuclease, divalent cation and/or the SSB to the solution comprising exonuclease-resistant primer may either be performed sequentially or simultaneously. In embodiments where the sequential addition is performed, the addition may be carried out in any particular order. For example, in some embodiments, the exonuclease and the divalent cation may be mixed first and then added to the primer solution followed by the SSB protein. In some other embodiments, the primer solution may be contacted with the SSB protein first and then the exonuclease and the divalent cation could be added.

After the decontamination step using the exonuclease, the exonuclease in the primer solution may be inactivated. The exonuclease may be inactivated by a variety of methods available in the art. In one specific embodiment, the exonuclease may be inactivated by thermal denaturation of the exonuclease. This may be achieved by incubating the decontaminated primer solution at a temperature at which the nuclease is not stable. The incubation is performed for a specified period of time that is sufficient to inactivate the exonuclease. In some embodiments, this may be achieved by incubating the decontaminated primer solution at temperatures at or above 65° C. In some embodiments, the decontaminated primer solution may be incubated at a temperature between 65° C. and about 95° C. The time that is sufficient to thermally inactivate the exonuclease may vary depending on the temperature used and the type of nuclease involved. Typically, the thermal inactivation may be performed for a time span of about 30 sec. to about 2 h. In some embodiments, the decontaminated primer solution may be incubated at about 85° C. for 15 min and then at about 95° C. for 5 min. The time span and the temperature may be optimized as required to thermally inactivate the exonuclease. In specific embodiments wherein the primer solution contains a DNA polymerase and/or endonuclease V along with other reagents in the exonuclease treatment step for removing contaminating nucleic acids, the DNA amplification reaction may be performed with or without inactivating the exonuclease. In embodiments wherein the inactivation step is not used, the quantity of exonuclease may be selected such that it does not interfere with the DNA amplification reaction. In embodiments wherein the inactivation step needs to be performed, the DNA polymerase, endonuclease V and exonuclease are either selected such that the exonuclease can selectively be inactivated without inactivating the DNA polymerase and/or endonuclease or the DNA polymerase and endonuclease V is added to the decontaminated primer solution only after deactivating the exonuclease that was used for decontamination.

Once substantially all the contaminating nucleic acid has been rendered inert, a DNA template to be amplified may be added to the decontaminated primer solution. At least one DNA polymerase having strand displacement activity, at least one endonuclease that is capable of nicking an inosine-containing strand of a double stranded DNA at a residue 3' to the inosine residue and free nucleotides are also added to the primer solution if they are not already present in the primer solution during the decontamination step. Removal of degraded contaminating nucleic acids from the decontaminated primer solution may not be required since they do not interfere with the DNA synthesis reaction. The DNA polymerase that could be employed for amplifying the DNA template may be a proofreading DNA polymerase or a non-proofreading DNA polymerase. In some specific embodiments, a combination of a proofreading DNA polymerase and a non-proofreading DNA polymerase may be used for efficient amplification of the DNA template.

In some embodiments, the DNA amplification reaction is performed under isothermal conditions. The reaction temperature during an isothermal amplification reaction condition may range 1° C., 5° C., or 10° C. from a set temperature. In some embodiments, the reaction temperature of DNA amplification is held at 45° C. (±1° C.). Thermally stable endonucleases and thermally DNA polymerases may be used depending upon the reaction temperature of DNA amplification reaction.

Any of the DNA polymerases known in the art may be employed for DNA amplification. DNA polymerases suitable for use in the inventive methods may demonstrate one or more of the following characteristics: strand displacement activity; the ability to initiate strand displacement from a nick; and/or low degradation activity for single stranded DNA. In some embodiments, the DNA polymerase employed may be devoid of one or more exonuclease activities. For example, the DNA polymerase may be a 3'→5' exonuclease-deficient DNA polymerase or the DNA polymerase may lack 5'→3' exonuclease activity. In some embodiments, the DNA polymerase may lack both 3'→5' and 5'→3' exonuclease activities (i.e., an exo (−) DNA polymerase). Exemplary DNA polymerases useful for the methods include, without limitation, Klenow, 5'→3' exonuclease-deficient Bst DNA polymerase (the large fragment of Bst DNA polymerase), 5'→3' exonuclease-deficient delta Tts DNA polymerase, exo (−) Klenow, or exo(−) T7 DNA polymerase (Sequenase™).

In some embodiments, a proofreading DNA polymerase may be used for DNA amplification reaction. In some specific embodiments, the solution containing proofreading DNA polymerase may also be decontaminated prior to its addition to the decontaminated primer solution. The decontamination of the proofreading DNA polymerase solution may be achieved by pre-treating it with a divalent cation (e.g., Mg2+ or Mn2+) in the absence of dNTPs. In one embodiment, a Phi29 DNA polymerase is employed and Phi29 DNA polymerase solution is decontaminated by incubating the Phi29 DNA polymerase solution with magnesium ions at a specified temperature for a sufficient period of time to render any contaminating nucleic acid inert prior to its addition to the decontaminated primer solution for carrying out the template DNA amplification.

Polymerase enzymes typically require divalent cations (e.g., $Mg^{+2}$, $Mn^{+2}$, or combinations thereof) for nucleic acid synthesis. Accordingly, one or more divalent cations may be added to the DNA amplification reaction mixture. For example, $MgCl_2$ may be added to the reaction mixture at a concentration range of 2 mM to 6 mM. Higher concentrations of $MgCl_2$ may be preferred when high concentrations (e.g., greater than 10 pmoles, greater than 20 pmoles, or greater than 30 pmoles) of inosine-containing primer are included in the reaction mixture.

In some embodiments, a mutant endonuclease V is included in the DNA amplification reaction mixture to nick the inosine-containing double stranded DNA. The mutant endonuclease V may be generated by any technique for genetic engineering or protein engineering including site-directed mutagenesis or artificial gene synthesis. The genetic engineering may include an alteration of one or more amino acid residues of a wild type endonuclease V. The alteration may include substitution, insertion and/or deletion of one or more amino acid residues of the wild type endonuclease V. Mutant endonuclease V may be generated by rational design of protein or by directed evolution. In some embodiments, a rationally designed, mutant endonuclease V enzyme is employed that has increased substrate binding, increased nicking efficiency, increased nicking specificity and/or increased nicking sensitivity. A mutant endonuclease V may also be designed such that the substrate binding is reversible. The mutant endonuclease V enzyme may then support repeated nicking by each enzyme, whereas the corresponding wild type enzyme may be capable of only a single round (or a few limited rounds) of nicking (for example, the wild type E. coli endonuclease V (SEQ ID NO: 1) remains bound to the DNA after nicking). Such mutant endonuclease V may be used in a reaction mixture in less than stoichiometric quantities to effect a nicking reaction. In some embodiments, conservative variants of the mutant endonuclease V may be used for the DNA amplification reaction. For example, further alteration of a mutant endonuclease V via substitution, deletion, and/or addition of a single amino acid or a small number (typically less than about ten) of amino acids may be a "conservative variant" if the physico-chemical properties of the altered mutant endonuclease V is similar to the original mutant endonuclease V. In some cases, the alteration may be a substitution of one amino acid with a chemically similar amino acid.

In some embodiments, a mutant endonuclease V that preferentially nicks the inosine-containing strand of a double stranded DNA at a position 3' to the inosine residue when the inosine residue is paired with a cytosine residue may be used. In some other embodiments, a mutant endonuclease V that preferentially nicks the inosine-containing strand of a double stranded DNA at a position 3' to the inosine residue when the inosine residue is paired with a thymine residue may be used. The mutant endonuclease V may have a higher efficiency than the wild type endonuclease V to nick the inosine-containing strand of the double stranded DNA when the inosine is paired with cytosine or thymine. Further, a mutant endonuclease V employed in the DNA amplification reaction may preferentially nick an inosine-containing strand of a double stranded DNA than an inosine-containing single stranded DNA. For example, Y75A E. coli mutant endonuclease V (SEQ ID NO: 2) nicks a double stranded DNA comprising an inosine residue better than a single stranded DNA comprising an inosine residue. In contrast, Y80A Tma mutant endonuclease V (SEQ ID NO: 6) nicks a single stranded DNA comprising an inosine residue better than a double stranded DNA comprising an inosine residue. Some mutant endonucleases may nick structures other than DNA sequences containing inosine residue while some others may be very specific to inosine-containing DNA sequences. For example, Tma and Afu endonucleases (SEQ ID NO: 3 and SEQ ID NO: 5) do not nick structures such as flaps and pseudo Y structures. In some embodiments, when there are multiple inosine residues in a double stranded DNA, the employed endonuclease V mutant may preferentially nick (often 1 or 2 nucleotides 3' to the inosine residue) the inosine residue that is paired with a cytosine residue than the inosine residue that is paired with a thymine residue. In some aspects, the endonuclease V mutant may nick a double stranded DNA containing base pair mismatches. The nicking may happen at the location of the base pair mismatch or at a location 3' to the base pair mismatch that is separated by one or more bases.

In some embodiments, a heat stable endonuclease V is used for the DNA amplification reaction. For example, in a DNA amplification assay, where thermal denaturation (either partial or full denaturation) of a target DNA is performed, a heat stable endonuclease V or a heat stable endonuclease V mutant may be preferred. In other embodiments where thermal denaturation of a target DNA is not required, a wild type endonuclease V or an endonuclease V mutant (e.g., Y75A mutant E. coli endonuclease V) that has maximum enzymatic activity at a relatively low temperature (e.g., 45° C.) may be used. For example, Y75A E. Coli endonuclease V mutant is inactivated by incubation at 50° C., whereas it retains its enzymatic activity at 37-45° C. Afu endonuclease V (both wild type (SEQ ID NO: 3) and Y75A mutant (SEQ ID NO: 4)) or Tma endonuclease V (both wild type (SEQ ID NO: 5) and Y80A mutant (SEQ ID NO: 6)) are generally more thermo stable than the E. coli endonuclease V (both wild type (SEQ ID NO: 1) and Y75A mutant (SEQ ID NO: 2)). In some embodiments where strand displacement DNA synthesis by DNA polymerase may be increased by incubation at an elevated temperature, an endonuclease V which functions at high temperature (e.g., 45-80° C.) may be used.

In some embodiments, a mutant E. coli endonuclease V is employed for DNA amplification reactions. The mutant E. coli endonuclease may be a Y75A mutant E. coli endonuclease V corresponding to SEQ ID NO: 2. This mutant is generated by replacing the Tyrosine (Y) residue at the $75^{th}$ position of a wild type E. coli endonuclease V (SEQ ID NO: 1) with an Alanine (A) residue. In some embodiments, a mutant Afu endonuclease Y74A (SEQ ID NO: 4) and/or its conservative variants is employed. The mutant Y74A Afu endonuclease is generated by substituting a Tyrosine (Y) residue at the $75^{th}$ position of a wild type Afu endonuclease V (SEQ ID NO: 3) with an alanine (A) residue.

Table 1 provides the sequences of wild type endonucleases and mutant endonuclease V enzymes.

TABLE 1

Sequences of wild type endonucleases, mutant endonucleases, template DNAs, and various primers

| | Ref. No. | Sequence (N-term-C-term; 5'→3') | Length |
|---|---|---|---|
| Wide Type *E. coli* endonuclease V | SEQ ID NO: 1 | MIMDLASLRAQQIELASSVIREDRLDKD PPDLIAGADVGFEQGGEVTRAAMVLLK YPSLELVEYKVARIATTMPYIPGFLSPRE YPALLAAWEMLSQKPDLVFVDGHGISH PRRLGVASHFGLLVDVPTIGVAKKRLCG KFEPLSSEPGALAPLMDKGEQLAWVWR SKARCNPLFIATGHRVSVDSALAWVQR CMKGYRLPEPTRWADAVASERPAFVRY TANQP | 223 |
| Y75A mutant *E. coli* endonuclease V | SEQ ID NO: 2 | MIMDLASLRAQQIELASSVIREDRLDKD PPDLIAGADVGFEQGGEVTRAAMVLLK YPSLELVEYKVARIATTMPAIPGFLSPRE YPALLAAWEMLSQKPDLVFVDGHGISH PRRLGVASHFGLLVDVPTIGVAKKRLCG KFEPLSSEPGALAPLMDKGEQLAWVWR SKARCNPLFIATGHRVSVDSALAWVQR CMKGYRLPEPTRWADAVASERPAFVRY TANQPLE | 225 |
| Wild Type Afu endonuclease V | SEQ ID NO: 3 | MLQMNLEELRRIQEEMSRSVVLEDLIPL EELEYVVGVDQAFISDEVVSCAVKLTFP ELEVVDKAVRVEKVTFPYIPTFLMFREG EPAVNAVKGLVDDRAAIMVDGSGIAHP RRCGLATYIALKLRKPTVGITKKRLFGE MVEVEDGLWRLLDGSETIGYALKSCRR CKPIFISPGSYISPDSALELTRKCLKGYKL PEPIRIADKLTKEVKRELTPTSKLK | 221 |
| Y74A mutant Afu endonuclease V | SEQ ID NO: 4 | MLQMNLEELRRIQEEMSRSVVLEDLIPL EELEYVVGVDQAFISDEVVSCAVKLTFP ELEVVDKAVRVEKVTFPAIPTFLMFREG EPAVNAVKGLVDDRAAIMVDGSGIAHP RRCGLATYIALKLRKPTVGITKKRLFGE MVEVEDGLWRLLDGSETIGYALKSCRR CKPIFISPGSYISPDSALELTRKCLKGYKL PEPIRIADKLTKEVKRELTPTSKLK | 221 |
| Wild Type Tma endonuclease V | SEQ ID NO: 5 | MDYRQLHRWDLPPEEAIKVQNELRKKI KLTPYEGEPEYVAGVDLSFPGKEEGLAV IVVLEYPSFKILEVVSERGEITFPYIPGLL APREGPLFLKAWEKLRTKPDVVVFDGQ GLAHPRKLGIASHMGLFIEIPTIGVAKSR LYGTFKMPEDKRCSWSYLYDGEEIIGCV IRTKEGSAPIFVSPGHLMDVESSKRLIKA FTLPGRRIPEPTRLAHIYTQRLKKGLF | 225 |
| Y80A mutant Tma endonuclease V | SEQ ID NO: 6 | MDYRQLHRWDLPPEEAIKVQNELRKKI KLTPYEGEPEYVAGVDLSFPGKEEGLAV IVVLEYPSFKILEVVSERGEITFPAIPGLL APREGPLFLKAWEKLRTKPDVVVFDGQ GLAHPRKLGIASHMGLFIEIPTIGVAKSR LYGTFKMPEDKRCSWSYLYDGEEIIGCV IRTKEGSAPIFVSPGHLMDVESSKRLIKA FTLPGRRIPEPTRLAHIYTQRLKKGLF | 225 |

In some embodiments the method for producing at least one amplicon based on a target DNA comprises the steps of (a) providing the target DNA; (b) providing a primer solution consisting essentially of an exonuclease-resistant, inosine-containing primer; (c) treating the primer solution with an exonuclease to remove any contaminating nucleic acids from the primer solution; (d) inactivating the exonuclease in the primer solution after the decontamination step (c); (e) generating a DNA amplification reaction mixture by mixing together the target DNA, the decontaminated primer solution, at least one 5'→3' exonuclease-deficient DNA polymerase having strand displacement activity, and at least one endonuclease that is capable of nicking a DNA at a residue 3' to an inosine residue; and (f) amplifying at least one portion of the target DNA using the DNA amplification reaction mixture of step (e) to produce the at least one amplicon. The primer solution may further comprise other nucleic acid amplification reagents such as dNTPs and amplification buffers. The primer solution may further comprise one or more of reagents such as formamide, SSB protein, ethylene glycol or Ficoll. However, in embodiments wherein the primer solution consists essentially of an exonuclease-resistant, inosine-containing primer the primer solution, the primer solution is devoid of amplicons, exonuclease-resistant oligonucleotides, inosine-containing oligonucleotides, or exonuclease-resistant, inosine-containing primers that are originated from previous amplification reactions (e.g., nucleic acid contaminants from prior amplification reactions).

The DNA amplification reaction mixture for nucleic acid amplification reaction may further include one or more reagents such as surfactants (e.g., detergents), blocking reagents (e.g., albumin), topoisomerase, reducing agents or buffers. Generally, these reagents are added to the primer solution, which contains the exonuclease-resistant, inosine-containing primer, before the decontamination step (e.g., prior to the treatment of the primer solution with an exonuclease to remove any contaminating nucleic acids). After the exonuclease treatment, the decontaminated primer solution (that contains exonuclease-resistant, inosine-containing primer that is to be used for the DNA amplification along with other added reagents) is then used for generating the nucleic acid amplification reaction mixture (with or without the inactivation of the exonuclease employed for decontamination). In some specific embodiments, all the reagents that is required for DNA amplification (except the target DNA itself) is added to the primer solution prior to the treatment of the primer solution with the exonuclease. In such embodiments, almost all of the contaminated DNA (except the ones coming from the target DNA solution) may be removed from the DNA amplification reaction mixture, thereby making target DNA amplification contamination-free.

Any buffers (e.g., Tris buffer, HEPES buffer) that results in a reaction pH between 6 and 9 may be used for DNA amplification reaction. In some embodiments, the pH of the nucleic acid amplification reaction mixture is 7.7. In some embodiments, buffers that enhance DNA stability (e.g., HEPES) may be used. Thermo labile buffers such as Tris-Borate, HEPES, and MOPS buffers may be disfavored in some specific DNA amplification reactions that employ thermal denaturation of a target DNA or thermal denaturation of the exonuclease after the decontamination step. Surfactants may be applied to the reaction tube before introducing the first component of the reaction mixture. Alternatively, as with other reagents, surfactants may be added to the to the primer solution prior to the decontamination step by the exonuclease. In some embodiments, the surfactant may be a detergent selected from Tween-20, NP-40, Triton-X-100, or combinations thereof. In some embodiments, 0.05% NP-40 and 0.005% Triton X-100 is used for the reaction. In some specific embodiments, the DNA amplification reaction buffer may comprise 25 mM Tris-Borate; 5 mM $MgCl_2$; 0.01% Tween; and 20% ethylene glycol. Blocking agents such as an albumin (e.g., BSA or HSA) may be included in the DNA amplification reaction mixture to bind to the surface of the reaction vessel (e.g., plastic microcentrifuge tube or microtiter plate) thereby increasing the relative amount target DNA that is available for reaction with the nucleases or polymerases. The DNA amplification reaction mixture may include at least one topoisomerase (e.g., a type 1 topoisomerase). The topoisomerase may be present in the reaction mixture at a final concentration of at least 0.1 ng/µL. In some embodiments, the DNA amplification reaction mixture may include at least one single stranded DNA binding protein (e.g., E. coli SSB, T4 gene 32 protein (T4 g32p), T7 gene 2.5 protein, Ncp7, recA, or combinations thereof). The single stranded DNA binding protein may be present in the reaction mixture at a final concentration of at least 0.1 ng/µL. The DNA amplification reaction mixture may also include one or more reducing agents such as dithiothreitol (DTT), 2-mercaptoethanol (βME), Tris(carboxyethyl) phosphine (TCEP), or 2-mercaptoethylamine (MEA) that reduces the oxidation of enzymes in the reaction mix and improves the quality and yield of the amplicons produced.

The amplicons produced by various embodiments of the present DNA amplification methods may be determined qualitatively or quantitatively by any of the existing techniques. For example, for a qualitative or quantitative assay, terminal-phosphate-labeled ribonucleotides may be used in combination with a phosphatase during/after DNA amplification reaction for color generation. In such embodiments, the terminal phosphate may be protected from dephosphorylation by using terminal-phosphate methyl esters of dNTPs or deoxynucleoside tetraphosphates.

In some embodiments, the amplicon production kit comprises at least one exonuclease-resistant, inosine-containing primer, at least one 5'→3' exonuclease-deficient DNA polymerase with strand displacement activity, and at least one endonuclease, which is capable of nicking DNA at a residue 3' to an inosine residue. The inosine residue of the inosine-containing primer is located at least 4 nucleotides downstream of the 5' terminal residue. In some embodiments, the inosine residue is located at the 3' penultimate position of the primer sequence. In some embodiments, the exonuclease-resistant, inosine-containing primer comprises at least one phosphorothioate linkage between the inosine residue at the penultimate 3' position and the 3' terminal residue. In some embodiments, the kit may further comprise reagents or a reagent solution required for performing a DNA synthesis reaction. The exonuclease-resistant, inosine-containing primer included in the kit may either be a specific primer, a partially random primer or a random primer. In some embodiments, the kit comprises multiple exonuclease-resistant, inosine-containing primers. In some embodiments the kit comprises at least one endonuclease V. The endonuclease V may either be a wild type endonuclease V or a mutant endonuclease V. In some embodiments, the kit comprises a Y75A mutant E. coli endonuclease V. The DNA polymerase included in the kit may be a Klenow, 5'→3' exonuclease-deficient Bst DNA polymerase (the large fragment of Bst DNA polymerase), 5'→3' exonuclease-deficient delta Tts DNA polymerase, exo (−) Klenow, or exo(−) T7 DNA polymerase (Sequenase™).

The kit may further comprise an SSB protein. Suitable SSB proteins that may be included in the kit include, but not limited to, but not limited to, extreme thermostable single stranded DNA-binding protein (ET SSB from New England Biolabs, MA), rec A (e.g., E. coli RecA), Tth RecA (RecA homolog isolated from *Thermus thermophilus* from New England Biolabs, MA), phage T4 gene-32 protein, T7 gene 2.5 protein, Ncp7, and E. coli SSB protein.

The kit may further comprise exonuclease that may be used to decontaminate the primer solution comprising the at least one exonuclease-resistant, inosine-containing primer. Suitable exonucleases that the kit may comprise are, for example, but not limited to, exonuclease I, exonuclease III, exonuclease VII, T7 gene-6 exonuclease, spleen exonuclease, T5 D15 exonuclease and lambda exonuclease. In some embodiments, the kit comprises exonuclease III. In some other embodiments, the kit may comprise a mixture of exonuclease I and exonuclease III. The combination of exonucleases may be provided in a single vessel or in multiple vessels, packaged together. The kit may further include an instruction manual detailing the specific components included in the kit and the protocols for using them in a de-contamination reaction or in a DNA amplification reaction or both.

Practice of the invention will be still more fully understood from the following examples, which are presented herein for illustration only and should not be construed as limiting the scope of the present invention as defined by the appended claims.

EXAMPLES

Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

All melting temperature values provided herein are determined according to the formula, $100.5+(41*(yG+zC-16.4)/(wA+xT+yG+zC))-(820/(wA+xT+yG+zC))+16.6*LOG10([Na+]+[K+])-0.56(\% EG)-0.32(\% G)-0.62(\% F)$ where w, x, y and z refer to the number of adenosine, cytosine, guanosine and thymidine residues, respectively, contained in the primer, Na+ refers to the sodium concentration (mM), K+ refers to the potassium concentration (mM), EG refers to the ethylene glycol concentration (%), G refers to the glycerol concentration (%), and F refers to the formamide concentration.

Tris-HCl and Tween 20 were obtained from Sigma Aldrich; dNTPs were obtained from GE Healthcare; and NaCl was obtained from Ambion. Volumes shown in the following Tables are in microliters unless otherwise indicated. Amplicons may be visualized and/or quantified using any of art-recognized techniques (e.g., electrophoresis to separate species in a sample and observe using an intercalating dye such as ethidium bromide, acridine orange, or proflavine). Amplicon production may also be tracked using optical methods (e.g., ABI Series 7500 Real-Time PCR machine) and an intercalating dye (e.g., SYBR Green I). The amplicons produced in the following examples were visualized using electrophoresis or optical techniques.

HET Buffer is 10 mM HEPES Buffer, pH 8, 0.1 mM EDTA and 0.1% (v/v) Tween 20. 10× denaturation buffer is 100 mM HEPES Buffer, pH 8.0, 1 mM EDTA, 0.1% (v/v) Tween 20 and 10 mg/ml BSA. 10× Reaction Buffer is 150 mM HEPES Buffer, pH 8, 30 mM magnesium chloride, 1 mM manganese sulphate, 2.5 mM dATP, 2.5 mM dCTP, 2.5 mM dGTP, 2.5 mM dTTP, 50 mM ammonium sulphate, 10 mM TCEP and 0.1% (v/v) Tween 20. Enzyme Dilution Buffer is 10 mM HEPES, pH 8, 1 mM TCEP, 0.5 mM EDTA, 0.01% (v/v) Tween 20 and 50% (v/v) glycerol. 5% (w/v) Ficoll 400 is equivalent to 5 g/100 ml of water.

Example 1

Endonuclease-Assisted Isothermal Amplification of a Template DNA

Endonuclease-assisted, isothermal amplification reaction has three reagent mixes that are prepared separately and then mixed together to create the final amplification reaction. These three reagent mixes are identified as denaturation mix, enzyme mix and reaction mix.

The denaturation mix is prepared by combining 0.5 µl 10× denaturation buffer, 1 µl of the desired target DNA template at the appropriate concentration, 0.5 µl 25% (v/v) formamide, 1 µl of an appropriate oligo mix containing nuclease-resistant primers and 2 µl of nuclease-free water for a final volume of 5 The denaturation mix is heated at 95° C. for two minutes and then placed at room temperature.

The enzyme mix is prepared by combining 0.34 µl of the Large fragment of Bst DNA polymerase (120 units/µl), 0.2 µl of E. coli SSB (5 µl/µl), 0.041 µl of mutant E. coli endonuclease V (6.23 mg/ml) and 0.419 µl of Enzyme Dilution Buffer for a final volume of 1 µl.

The reaction mix is prepared by combining 1 µl of 10× Reaction Buffer, 2 µl ethylene glycol, 1 µl of 50% (v/v) Ficoll 400 and 1 µl of the Enzyme mix for a final volume of 5 µl.

A complete Ping Pong reaction is assembled by pre-heating separately both the Denaturation mix and Reaction mix at 45° C. for 30 seconds. Both mixes are then combined and incubated at 45° C. for one hour.

Following incubation, the amplification is analyzed by gel electrophoresis using a 15% Acrylamide TBE-Urea gel (Invitrogen) Immediately prior to gel loading, 3 µl of a completed Ping Pong reaction is combined with 6 µl Gel Loading Buffer II (Invitrogen) and heat denatured at 95° C. for two minutes followed by immediate quenching on ice. 5 µl of this heat-denatured Ping Pong reaction is then loaded in one well of the gel. Electrophoresis is accomplished according to the manufacturer's (Invitrogen) instructions. Once electrophoresis is complete, the gel is stained with a 20× solution of SYBR Gold (Invitrogen) for 15 minutes and then scanned for fluorescein with a Typhoon 9410 Variable Mode Imager (GE Healthcare).

Example 2

Endonuclease-Assisted Isothermal Amplification of a Template DNA Using Exonuclease-Resistant, Inosine-Containing Primers The primers used in Endonuclease-assisted isothermal amplification contain an inosine as the penultimate 3' base. Endonuclease V recognizes inosine as a non-natural base and nicks the DNA strand containing the inosine residue at one base 3' to the lesion. This example demonstrates the enhanced amplification kinetics using a nuclease-resistant primer, wherein the phosphate bond between the inosine reside and the terminal 3' base has been phosphorothioated.

Sequences for six forward and five reverse primers were identified in the 5' region of the Mycobacterium tuberculosis rpoB gene. Two sets of these 11 primers were synthesized, one set without phosphorothioation and the other set with phosphorothioation between the inosine and the terminal 3' base of each primer. TABLE 2 and TABLE 3 provide the sequences of the various primers used in the examples.

TABLE 2

Non-phosphorothioated primers without phosphorothioation between the inosine and the terminal 3 base of each primer

| Primer Name | Ref. No. | Sequence (5'→3') | Length |
|---|---|---|---|
| IA TBropB F1 | SEQ ID NO: 40 | ACAGCCGCTAGTCCTAIT | 18 |
| IA TBropB F2 | SEQ ID NO: 7 | CCCGCAAAGTTCCTCIA | 17 |

TABLE 2-continued

Non-phosphorothioated primers without phosphorothioation between the inosine and the terminal 3 base of each primer

| Primer Name | Ref. No. | Sequence (5'→3') | Length |
|---|---|---|---|
| IA TBrpoB F3n | SEQ ID NO: 8 | ACCGGGTCTCCT TCIC | 16 |
| IA TBrpoB F4 | SEQ ID NO: 9 | GCTGCGCGAACCACTTIA | 18 |
| IA TBrpoB F5 | SEQ ID NO: 10 | CCGTACCCGGAGCIC | 15 |
| IA TBrpoB F6 | SEQ ID NO: 11 | CAGATTCCCGCCAGAIC | 17 |
| IA TBropB R2 | SEQ ID NO: 12 | GGCGAACCGATCAIC | 15 |
| IA TBropB R3 | SEQ ID NO: 13 | CGGCGGATTCGCIC | 14 |
| IA TBrpoB R4 | SEQ ID NO: 14 | GGTTGACATCACCCCIC | 17 |
| IA TBrpoB R5 | SEQ ID NO: 15 | GAGCACCTCTTCCAGIC | 17 |
| IA TBrpoB R6 | SEQ ID NO: 16 | CGATCGGAGACAGCTCIT | 18 |

TABLE 3

Phosphorothioated primers with phosphorothioation (* represents phosphorothioate linkage) between the inosine and the terminal 3' base of each primer.

| Primer Name | Ref. No. | Sequence (5'→3') | Length |
|---|---|---|---|
| IA TBropB F1* | SEQ ID NO: 17 | ACAGCCGCTAGTCCTAI*T | 18 |
| IA TBrpoB F2* | SEQ ID NO: 18 | CCCGCAAAGTTCCTCI*A | 17 |
| IA TBrpoB F3n* | SEQ ID NO: 19 | ACCGGGTCTCCT TCI*C | 16 |
| IA TBrpoB F4* | SEQ ID NO: 20 | GCTGCGCGAACCACTTI*A | 18 |
| IA TBrpoB F5* | SEQ ID NO: 21 | CCGTACCCGGAGCI*C | 15 |
| IA TBrpoB F6* | SEQ ID NO: 22 | CAGATTCCCGCCAGAI*C | 17 |
| IA TBropB R2* | SEQ ID NO: 23 | GGCGAACCGATCAI*C | 15 |
| IA TBropB R3* | SEQ ID NO: 24 | CGGCGGATTCGCI*C | 14 |
| IA TBrpoB R4* | SEQ ID NO: 25 | GGTTGACATCACCCCI*C | 17 |
| IA TBrpoB R5* | SEQ ID NO: 26 | GAGCACCTCTTCCAGI*C | 17 |
| IA TBrpoB R6* | SEQ ID NO: 27 | CGATCGGAGACAGCTCI*T | 18 |

To generate the non-phosphorothioated primer set, 4.00 µL IA TBrpoB F1 (629 pmol/µL), 3.16 µL IA TBrpoB F2 (793 pmol/µL), 3.64 µL IA TBrpoB F3n (686 pmol/µL), 3.50 µL IA TBrpoB R2 (715 pmol/µL), 3.28 µl IA TBrpoB R3 (762 pmol/µL), 5.74 µL IA TBrpoB F4 (436 pmol/L), 2.84 µL IA TBrpoB F5 (880 pmol/µL), 4.17 µL IA TBrpoB F6 (599 pmol/µL), 4.94 µL IA TBrpoB R4 (506 pmol/µL), 4.15 µL IA TBrpoB R5 (602 pmol/µL) and 5.63 µL IA TBrpoB R6 (444 pmol/µL) was mixed with 204.95 µL HE(0.1)T buffer (Total Volume=250 µL)

To generate the phosphorothioated primer set, 3.32 µL IA TBrpoB F1* (754 pmol/µL), 2.72 µL IA TBrpoB F2* (920 pmol/µL), 2.83 µL IA TBrpoB F3* (883 pmol/µL), 4.68 µL IA TBrpoB F4* (534 pmol/µL), 1.72 µL IA TBrpoB F5* (1451 pmol/µL), 1.76 µL IA TBrpoB F6* (1417 pmol/µL), 2.72 µL IA TBrpoB R2* (920 pmol/µL), 1.80 µL IA TBrpoB R3* (1392 pmol/µL), 1.51 µL IA TBrpoB R4* (1652 pmol/µL), 1.79 µL IA TBrpoB R5* (1398 pmol/µl), and 7.00 µL IA TBrpoB R6* (358 pmol/µL) was mixed with 218.15 µL HE(0.1)T buffer (Total Volume=250 µL)

Figure 3:
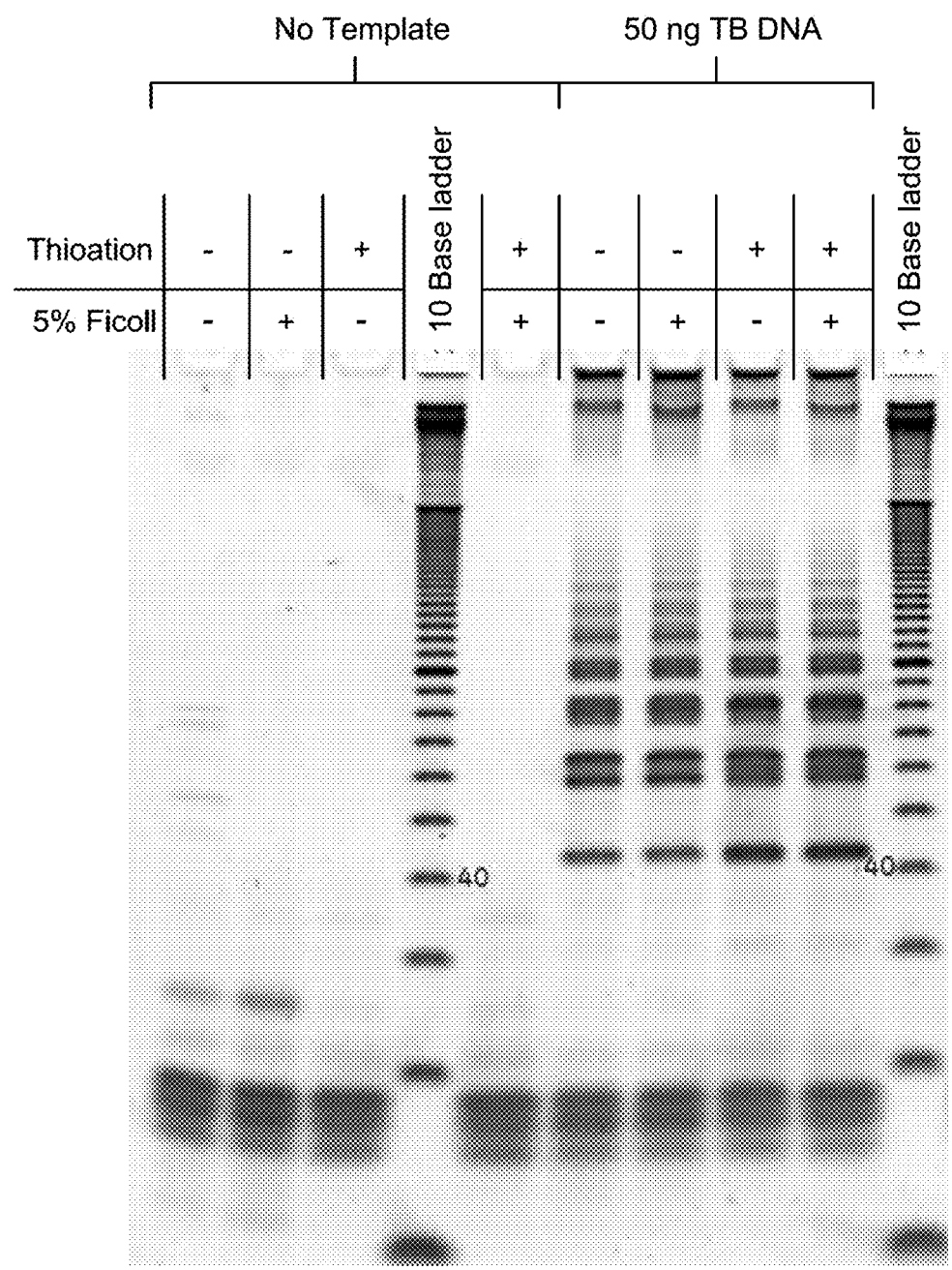
FIG. 3 illustrates an example of the effect of exonuclease-resistant, inosine-containing primer on endonuclease-assisted template DNA amplification.
Figure 4:
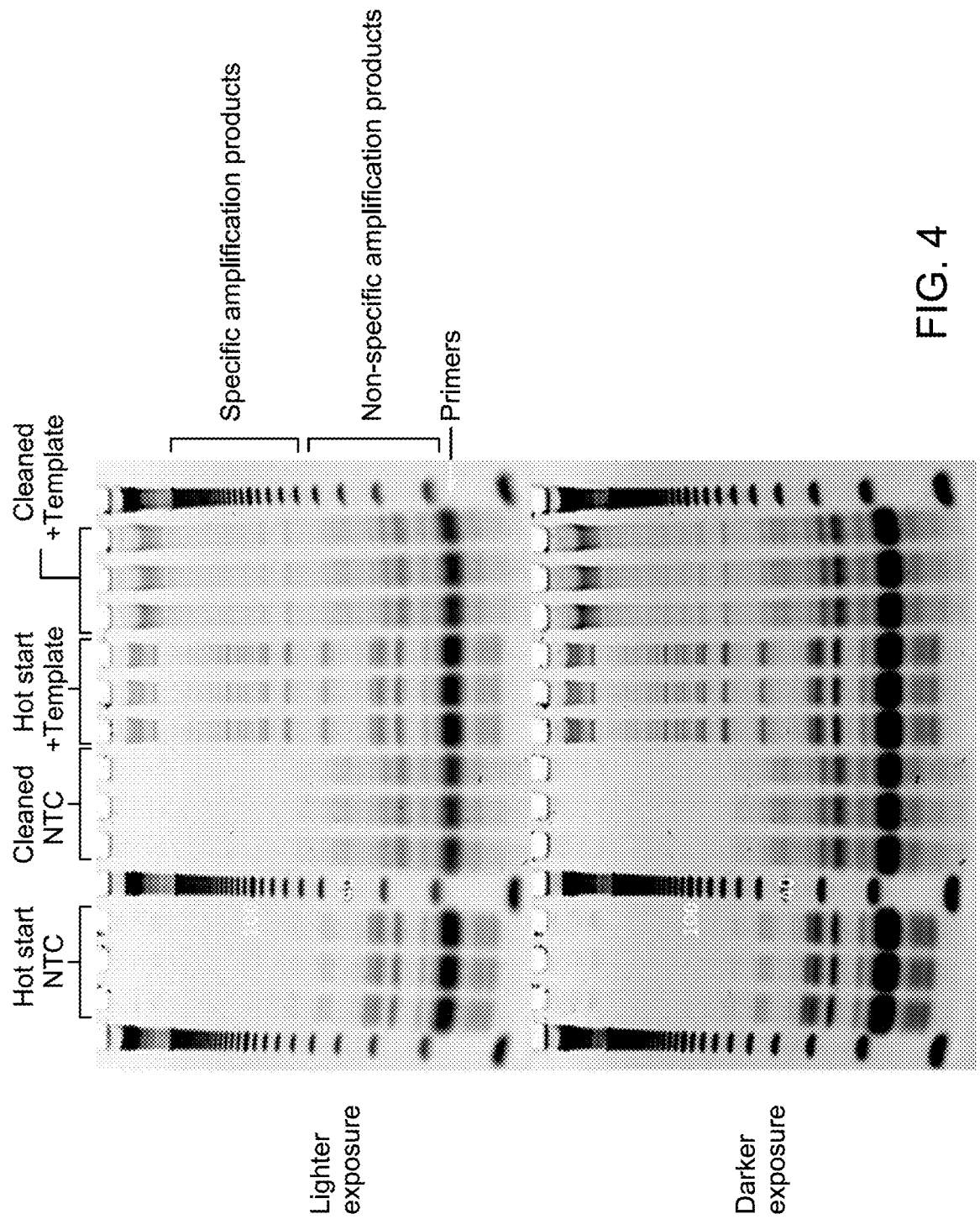
FIG. 4 illustrates an example of the effect of the removal of contaminating nucleic acids by exonuclease treatment of amplification reagents prior to endonuclease-assisted template DNA amplification.

Each primer set was then used in an endonuclease-assisted isothermal amplification reaction prepared and analyzed as in Example 1. The final concentration of each oligonucleotide primer in the Ping Pong reaction was 10 pmol. As depicted in FIG. 3, use of nuclease-resistant primers (i.e., primer set containing phosphorothioation) increase the yield of endonuclease-assisted isothermal amplification reaction products by about a factor of two.

Example 3

Endonuclease-Assisted Isothermal Amplification of a Template DNA Using Contamination-Free Reagents In this Example, all Ping Pong reagents, except, the DNA polymerase, mutant Endonuclease V and the human genomic DNA templates are decontaminated to remove any exogenous DNA by a pre-amplification incubation step with exonucleases. In this example embodiment, 11 ng of human genomic DNA is used as the template in an amplification reaction and exonuclease-resistant, inosine-containing oligonucleotides are used as the primers. For this example, exonuclease I (Exo I) and exonuclease III (Exo III) were first incubated with the appropriate reagents for a certain time interval and then killed by heating. The cleaned reagents were then incorporated into a Ping Pong reaction.

A mixture containing 1.25 µL exonuclease I (New England Biolabs, 0.25 Units/µL), 1 µL exonuclease III (New England Biolabs, 1 Unit/µL) and 97.95 µL Enzyme Dilution Buffer was prepared. One microliter of this exonuclease mixture was added to 0.5 µL Denaturation Buffer, 1 µL 10× Reaction Buffer, 0.5 µL 25% (v/v) formamide, 0.2 µL SSB, 0.419 µL Enzyme Dilution Buffer, 2 µL ethylene glycol, 1 µL 50% (v/v) Ficoll 400, 1 µL of p53 Oligo Mix (phosphorothioated primers employed for p53 amplification as listed in TABLE 2) and 1 µL water for a final volume of 8.619 µL. The cleaning reaction was incubated at 37° C. for 30 minutes to allow the exonucleases to degrade any contaminating DNA and then incubated at 80° C. for 30 minutes to deactivate the exonucleases. The cleaned reagents were stored at +4° C. until required.

(NTC)). Control reactions without cleaning were prepared as in Example 2. All reactions were incubated and analyzed as in Example 2. FIG. 1 shows that cleaning of the Ping Pong reagents including exonuclease-resistant inosine containing primer with an exonuclease eliminates non-specific amplification products.

The above detailed description is exemplary and not intended to limit the invention of the application and uses of the invention. Throughout the specification, exemplification of specific terms should be considered as non-limiting examples. The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the specification and attached claims are approximations that

TABLE 4

Phosphorothioated primers (* represents phosphorothioate linkage) employed for p53 amplification.

| Primer Name | Ref. No. | Sequence (5'→3') | Length |
| --- | --- | --- | --- |
| IA p53 F1* | SEQ ID NO: 28 | GCCTCGCCTCCCGAI*T | 16 |
| IA p53 F2* | SEQ ID NO: 29 | CTGGGATTACAGGCAT I*C | 18 |
| IA p53 F4* | SEQ ID NO: 30 | CTCCCGGGTTCAAGCI*A | 17 |
| IA p53 F5* | SEQ ID NO: 31 | GAGATCTCAGCTCACCI*C | 18 |
| IA p53 F6* | SEQ ID NO: 32 | CAGGCTGGAGTGTAAT I*G | 18 |
| IA p53 F7* | SEQ ID NO: 33 | GACGGAGTTTCACTCTTI*T | 19 |
| IA p53 R2* | SEQ ID NO: 34 | CTGAGGTCGGGAGTTTI*A | 18 |
| IA p53 R3* | SEQ ID NO: 35 | GAGGCCAAGGCGAGTI*I | 17 |
| IA p53 R4* | SEQ ID NO: 36 | GGCGCAGTGGCTCACI*A | 17 |
| IA p53 R5* | SEQ ID NO: 37 | AAAATGGGGTAAGGGGI*C | 18 |
| IA p53 R6* | SEQ ID NO: 38 | ACCCCCGTCAAACTCAI*T | 18 |
| IA p53 R7* | SEQ ID NO: 39 | GTCATATACTCAGCCCTI*C | 19 |

To generate the phosphorothioated primer set for p53 gene segment amplification, 5.96 µL IA p53 F1* (839 pmol/µL), 6.05 µL IA p53 F2* (826 pmol/µL), 7.40 µL IA p53 F3* (676 pmol/µL), 6.55 µL IA p53 F4* (763 pmol/µL), 10.99 µL IA p53 F5* (455 pmol/µL), 8.50 µL IA p53 F6* (588 pmol/µL), 6.17 µL IA p53 R1* (811 pmol/µL), 11.24 µL IA p53 R2* (445 pmol/µL), 15.38 µL IA p53 R3* (325 pmol/µL), 4.81 µL IA p53 R4* (1040 pmol/µL), 4.68 µL IA p53 R5* (1069 pmol/µL), 8.05 µL IA p52 R6* (621 pmol/µL), was mixed with 404.22 µL 0.01% Tween 20 (Total Volume=500 µL)

0.34 µL of the Large Fragment of Bst DNA polymerase and 0.041 µL of mutant Endonuclease V were added to the cleaned reagents along with either 1 µl (11 ng; ~1500 copies) of human genomic DNA or water (no template controls may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between.

The invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention described herein. While only certain features of the invention have been illustrated and described herein, it is to be understood that one skilled in the art, given the benefit of this disclosure, will be able to identify, select, optimize or modify suitable conditions/parameters for using the methods in accordance with the principles of the present invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the true spirit of the present invention. Further, all changes that come within the meaning and range of equivalency of the claims are intended to be embraced therein.

---

The invention claimed is:

1. A method of producing at least one amplicon based on a target DNA comprising:
   (a) providing the target DNA;
   (b) providing a primer solution comprising at least one exonuclease-resistant, inosine-containing primer, wherein said inosine-containing primer comprises at least one inosine residue or inosine analogue in its sequence;
   (c) generating a DNA amplification reaction mixture by mixing together the target DNA, the primer solution, at least one 5'→3' exonuclease-deficient DNA polymerase having a strand displacement activity, and at least one endonuclease that is capable of nicking an inosine-containing strand of a double stranded DNA at a residue 3' to an inosine residue or inosine analogue; and
   (d) incubating the DNA amplification reaction mixture to amplify at least one portion of the target DNA using the at least one exonuclease-resistant, inosine-containing primer to produce the at least one amplicon, wherein the nuclease-resistant, inosine-containing primer comprises a phosphorothioate linkage at the 3' side, or both the 3' and 5' side of and adjacent to the inosine residue or inosine analogue.

2. The method claim 1, wherein the primer solution further comprises free deoxynucleotide triphosphates (dNTPs).

3. The method of claim 2, wherein the primer solution further comprises DNA amplification buffer, formamide, single stranded DNA binding protein, ethylene glycol, Ficoll or combinations thereof.

4. The method of claim 1 further comprising decontaminating the primer solution, prior to generating the DNA amplification reaction mixture, by treating the primer solution with an exonuclease to remove any contaminating nucleic acids.

5. The method of claim 4, further comprising inactivating the exonuclease in the primer solution after removal of any contaminating nucleic acids prior to generating the DNA amplification reaction mixture, and wherein optionally the target DNA is amplified under isothermal conditions.

6. The method of claim 1, wherein the inosine residue or inosine analogue of the nuclease-resistant, inosine-containing primer is located at least 4 nucleotides downstream of the 5' terminal nucleotide.

7. The method of claim 6, wherein the inosine residue or inosine analogue of the nuclease-resistant, inosine-containing primer is located at the penultimate 3' position.

8. The method of claim 1, wherein the inosine-containing primer comprises at least 2 adjacent inosine residues or inosine analogues, wherein optionally the inosine residues are located both at the penultimate 3' position and the 3' terminal end of the inosine-containing primer.

9. The method of claim 1, wherein:
   i) the at least one 5'→3' exonuclease-deficient DNA polymerase is selected from 5'→3' exonuclease-deficient T7 DNA polymerase, 5'→3' exonuclease-deficient Bst DNA polymerase, 5'→3' exonuclease-deficient Klenow, 5'→3' exonuclease-deficient delta Tts DNA polymerase, or combinations thereof;

ii) the primer solution comprises at least one inosine-containing forward primer and at least one inosine-containing reverse primer, wherein both the forward primer and the reverse primer are exonuclease-resistant; or iii) the at least one nuclease-resistant, inosine-containing primer comprises an extender template.

\* \* \* \* \*